(12) United States Patent
Neale et al.

(10) Patent No.: US 12,258,221 B2
(45) Date of Patent: Mar. 25, 2025

(54) FOOD PRODUCT QUALITY CONTROL SYSTEM

(71) Applicant: ISHIDA EUROPE LIMITED, Birmingham (GB)

(72) Inventors: Graham Neale, Bournemouth (GB); Lee Vine, Poole (GB)

(73) Assignee: ISHIDA EUROPE LIMITED, Birmingham (GB)

( * ) Notice: Subject to any disclaimer, the term of this patent is extended or adjusted under 35 U.S.C. 154(b) by 224 days.

(21) Appl. No.: 17/790,441

(22) PCT Filed: Jan. 28, 2021

(86) PCT No.: PCT/GB2021/050197
§ 371 (c)(1),
(2) Date: Jun. 30, 2022

(87) PCT Pub. No.: WO2021/152313
PCT Pub. Date: Aug. 5, 2021

(65) Prior Publication Data
US 2023/0093613 A1 Mar. 23, 2023

(30) Foreign Application Priority Data
Jan. 31, 2020 (GB) .................................. 2001358

(51) Int. Cl.
*B65G 47/64* (2006.01)
*A22C 17/00* (2006.01)
(Continued)

(52) U.S. Cl.
CPC ........ *B65G 47/647* (2013.01); *A22C 17/0073* (2013.01); *B65G 21/12* (2013.01);
(Continued)

(58) Field of Classification Search
CPC .... B65G 47/647; B65G 21/12; B65G 41/001; A22C 17/0073; G01N 23/083; G01N 23/18; G01N 33/02
See application file for complete search history.

(56) References Cited

U.S. PATENT DOCUMENTS

| | | | | |
|---|---|---|---|---|
| 5,078,255 A | * | 1/1992 | Haley | B65G 47/647 198/369.2 |
| 6,708,813 B2 | * | 3/2004 | Takahashi | B65G 47/647 198/813 |

(Continued)

FOREIGN PATENT DOCUMENTS

| | | | | |
|---|---|---|---|---|
| CN | 104495277 A | * | 4/2015 | B65G 21/12 |
| CN | 205982135 U | * | 2/2017 | |

(Continued)

OTHER PUBLICATIONS

Jaime Alboim: Thermo Scientific NextGuard X-Ray Detection System, Foreign Object Detection for a Wide Variety of Food Products, 4 pages (Feb. 18, 2016). URL:https://www.slideshare.net/JaimeAlboim/nextguardbrochureweb [retrieved on Apr. 19, 2021].

(Continued)

*Primary Examiner* — Gene O Crawford
*Assistant Examiner* — Abby A Jorgensen
(74) *Attorney, Agent, or Firm* — SQUIRE PATTON BOGGS (US) LLP

(57) ABSTRACT

A food product quality control system is provided. The system comprises a support structure, an inspection unit for detecting at least one property of a food product supplied to the inspection unit, the inspection unit being mounted on the support structure, and a conveyor system for conveying a food product through and/or past the inspection unit, the conveyor system being mounted on the support structure. The conveyor system comprises a conveying apparatus carried on a frame. The frame is movably mounted to the (Continued)

support structure such that the frame may move relative to the inspection unit between an operation position, at which the frame is laterally aligned with the inspection unit such that food product may be conveyed through and/or past the inspection unit, and a maintenance position, at which the frame is laterally offset from the inspection unit.

20 Claims, 14 Drawing Sheets

(51) Int. Cl.
    *B65G 21/12*     (2006.01)
    *B65G 41/00*     (2006.01)
    *G01N 23/083*     (2018.01)
    *G01N 23/18*     (2018.01)
    *G01N 33/02*     (2006.01)

(52) U.S. Cl.
    CPC ......... *B65G 41/001* (2013.01); *G01N 23/083* (2013.01); *G01N 23/18* (2013.01); *G01N 33/02* (2013.01)

(56) References Cited

U.S. PATENT DOCUMENTS

| | | | |
|---|---|---|---|
| 2003/0123968 A1* | 7/2003 | Derenthal | B65B 23/14 414/790 |
| 2005/0287252 A1 | 12/2005 | Schrock et al. | |
| 2012/0247920 A1 | 10/2012 | Peters et al. | |
| 2012/0261231 A1 | 10/2012 | Eiserloh et al. | |
| 2014/0220197 A1 | 8/2014 | Hocker et al. | |
| 2019/0154599 A1* | 5/2019 | Kaminski | G01N 23/18 |

FOREIGN PATENT DOCUMENTS

| | | | | | |
|---|---|---|---|---|---|
| CN | 107140379 A | * | 9/2017 | ............ | B65G 15/58 |
| CN | 107758219 A | * | 3/2018 | ............ | B65G 21/12 |
| CN | 109018855 A | * | 12/2018 | ............ | B65G 21/12 |
| CN | 208705342 U | * | 4/2019 | | |
| EP | 0 225 810 A1 | | 6/1987 | | |
| EP | 826614 A2 | * | 3/1998 | ......... | B65G 47/5113 |
| EP | 1 256 529 A1 | | 11/2002 | | |
| EP | 1304562 A1 | * | 4/2003 | ............ | G01N 23/04 |
| JP | 2002-250703 A | | 9/2002 | | |
| JP | 2006-335466 A | | 12/2006 | | |
| JP | 2007-106523 A | | 4/2007 | | |
| WO | WO 2001/022071 A2 | | 3/2001 | | |
| WO | WO 2003/087787 A1 | | 10/2003 | | |
| WO | WO 2013/023778 A1 | | 2/2013 | | |
| WO | WO-2015003750 A1 | * | 1/2015 | ......... | A22C 17/0073 |
| WO | WO 2017/191465 A2 | | 11/2017 | | |
| WO | WO-2017213146 A1 | * | 12/2017 | ............ | G01N 23/04 |
| WO | WO-2021163751 A1 | * | 8/2021 | | |

OTHER PUBLICATIONS

International Report on Patentability for International Patent Application PCT/GB2021/050197, dated Apr. 8, 2022, 23 pages.
International Search Report for International Patent Application PCT/GB2021/050197, dated Jul. 23, 2021.
Written Opinion of International Searching Authority for International Patent Application PCT/GB2021/050197, dated Jul. 23, 2021.
Notice of Reasons for Refusal dated Oct. 1, 2024 issued in corresponding Japanese Patent Application No. 2022-545083, with English language machine translation thereof.

* cited by examiner

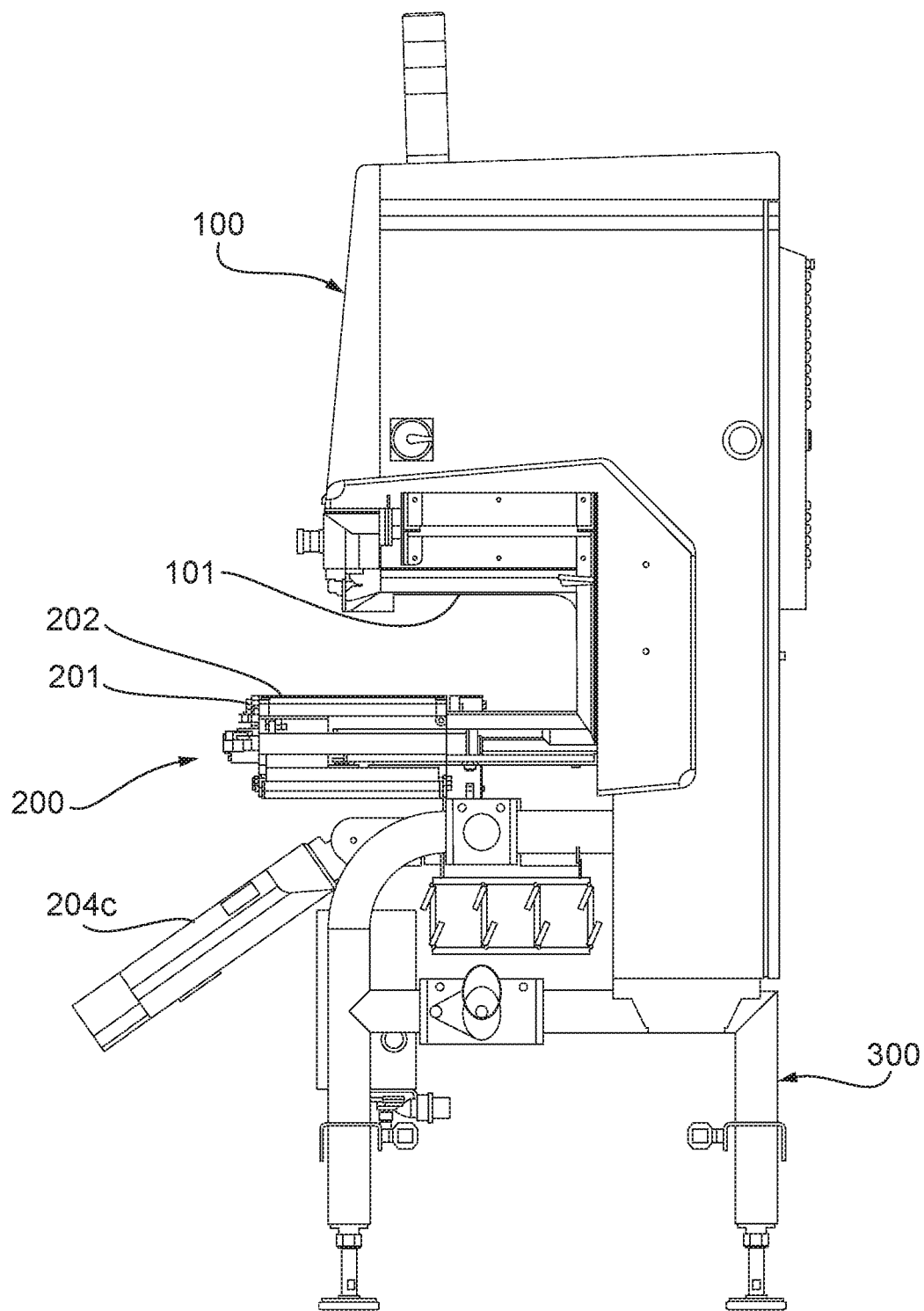

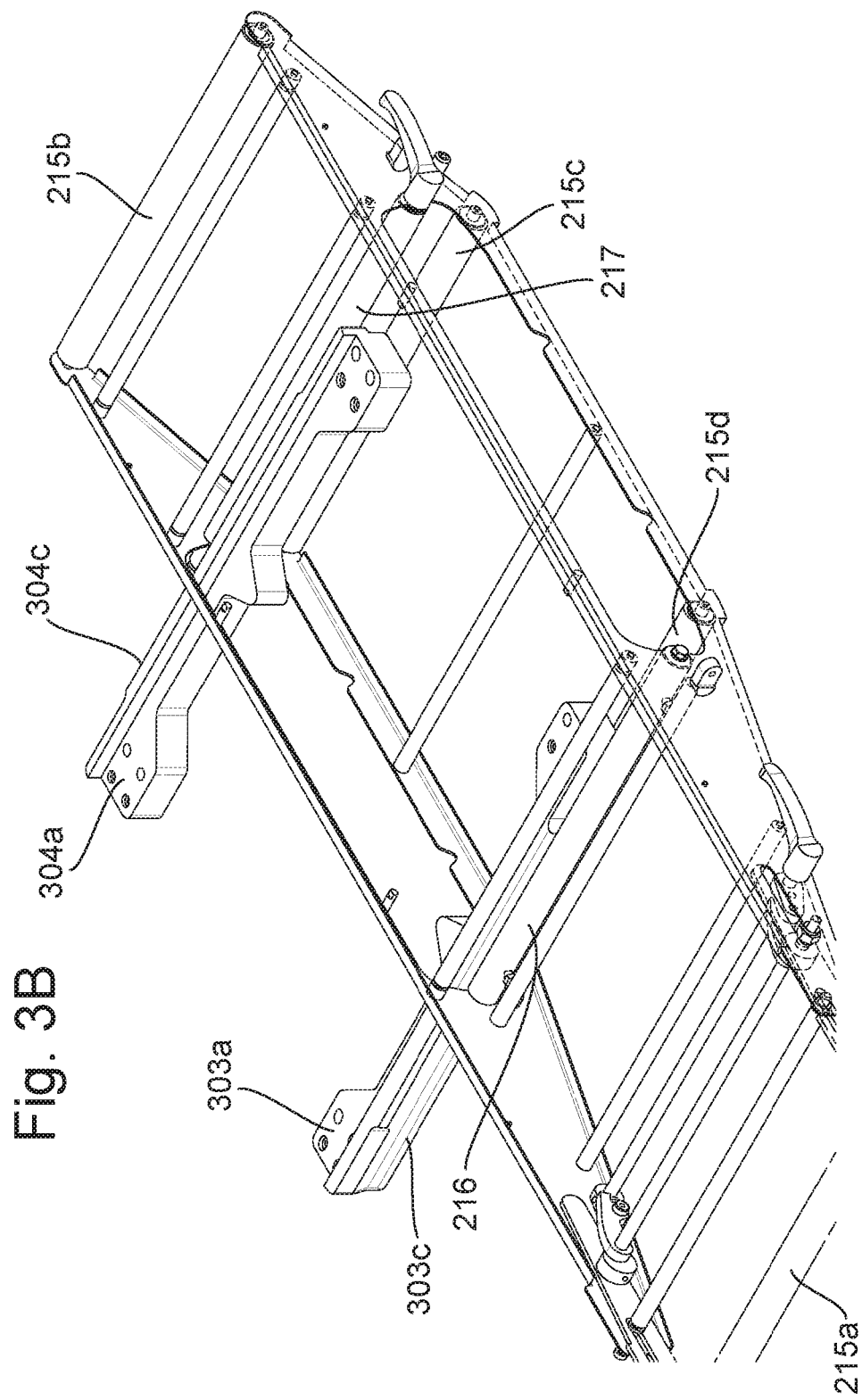

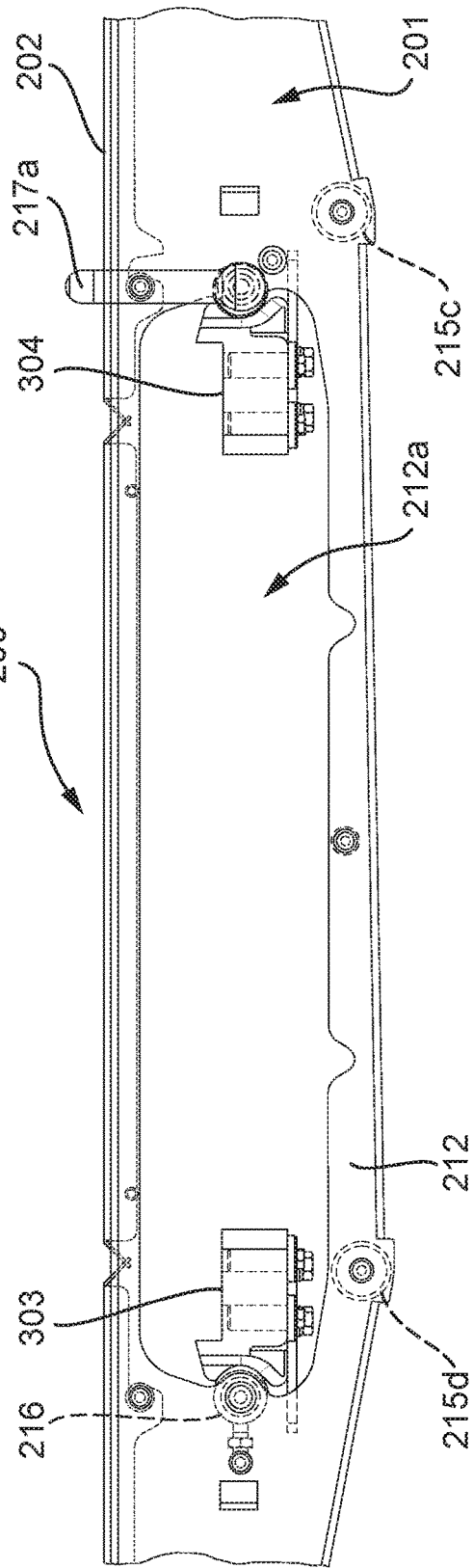
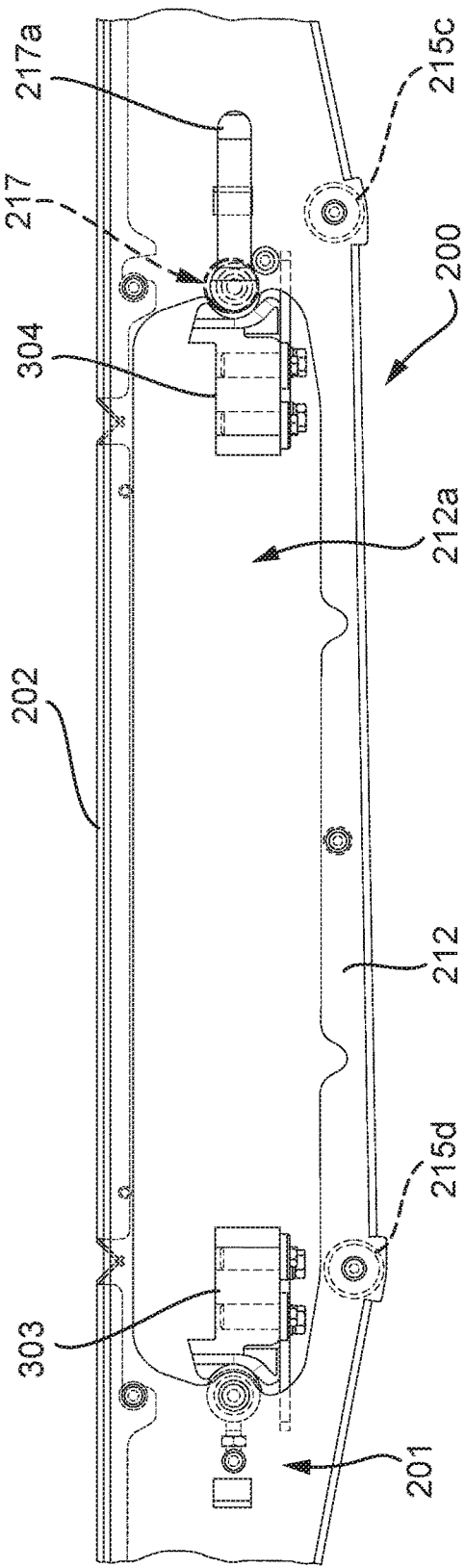

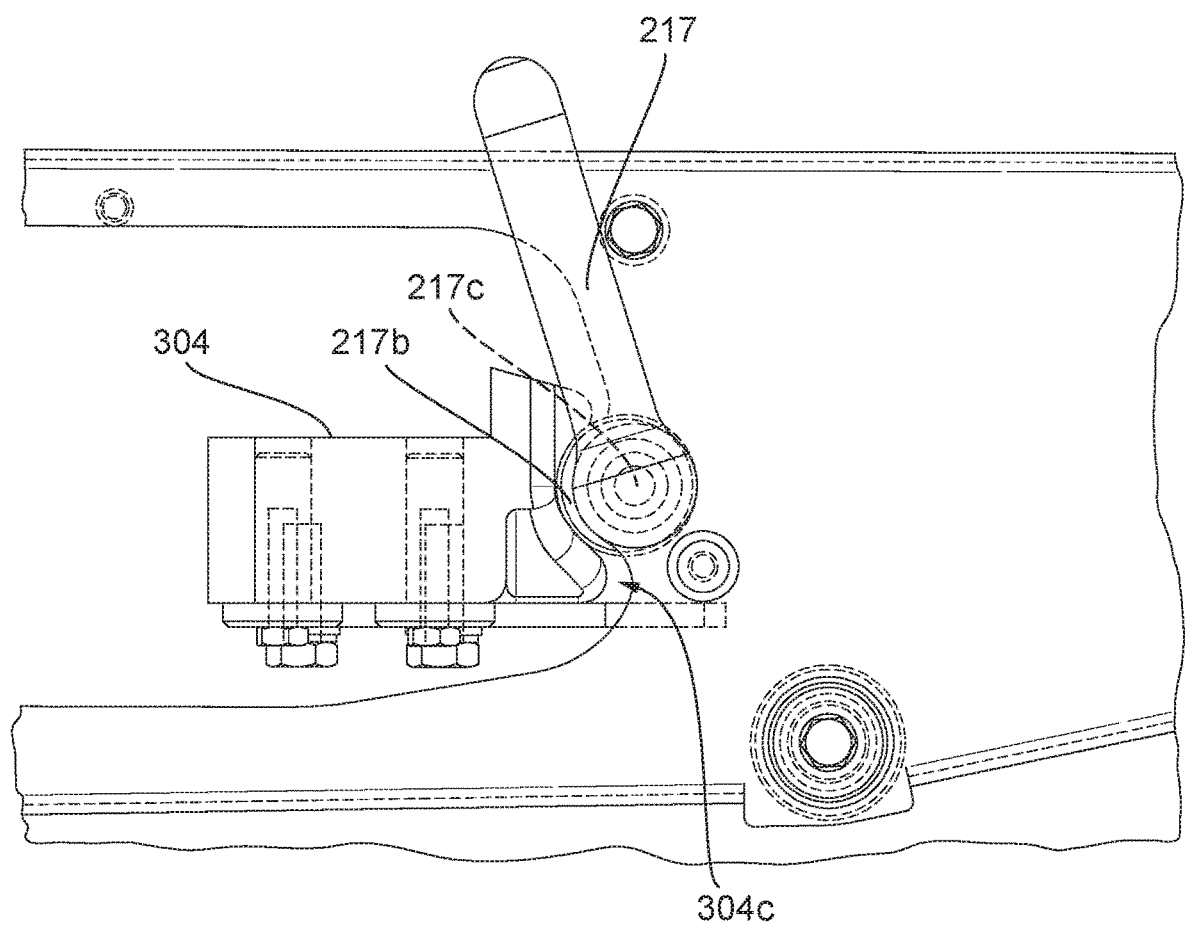

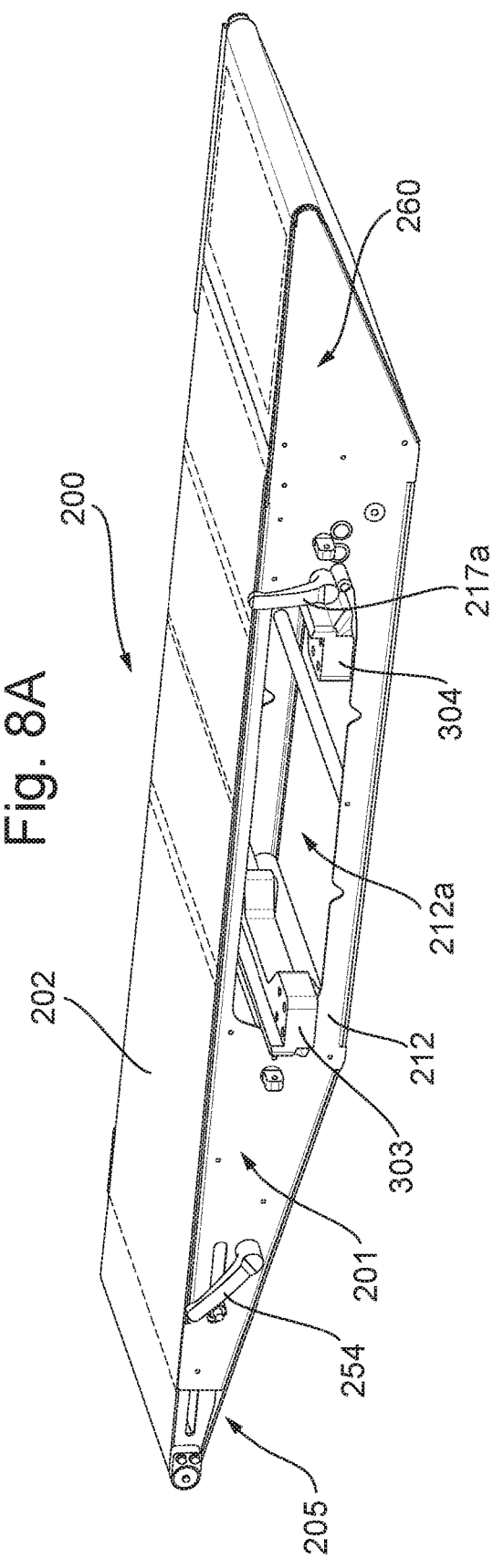
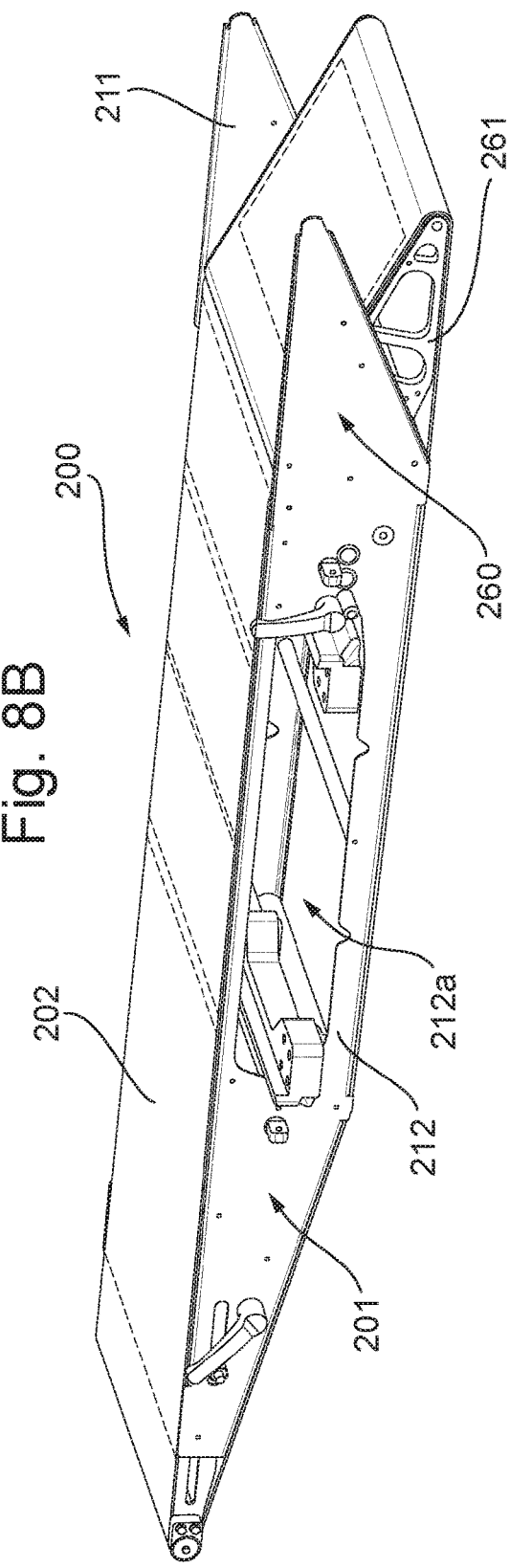

FOOD PRODUCT QUALITY CONTROL SYSTEM

CROSS-REFERENCE TO RELATED APPLICATIONS

This application is a national-stage filing under 37 USC 371(c) of International Application No. PCT/GB2021/050197, filed Jan. 28, 2021, which claims priority to, and the benefit of, Great Britain Patent Application GB2001358.7 filed Jan. 31, 2020, the entire contents of each of which are herein incorporated by reference in their entirety for all purposes.

FIELD OF THE INVENTION

The present invention relates to food product quality control systems and in particular those with integrated conveyor systems that may require regular cleaning or maintenance. Such systems will typically be used for inspecting food products, which may include packaged or unpackaged food items, such as items of poultry.

BACKGROUND TO THE INVENTION

Food product quality control is an essential part of the food industry. Systems for carrying out quality control include imaging systems, such as X-ray or visual inspection units, weighing systems that weigh food products, and leak inspection systems that test packaged food items for breaches in their container. All of these systems typically require the food products to conveyed through or past a fixed inspection unit and so will typically be coupled with a conveyor system that conveys the food products. Furthermore, with tolerances for error being so small, it is often important to fix the inspection unit relative to the conveyor. For example, an X-ray unit will require high positional accuracy in order to operate effectively, as will leak inspection systems, which could fail to detect breaches in sealed containers if not properly located.

With such food product quality control systems, it is important to be able to clean or perform maintenance on both the inspection unit and the conveyor on a regular basis. However, with the inspection unit and conveyor in such close proximity and often fixed to one another, cleaning and maintenance can be difficult and time consuming. In the food industry, extended periods of downtime for cleaning and maintenance can have a big impact on the overall throughput of a wider food processing system and so it is important to ensure that cleaning and maintenance can be performed quickly and effectively.

It is therefore desirable to provide a food product quality control system in which cleaning and maintenance is facilitated.

SUMMARY OF THE INVENTION

In accordance with a first aspect of the invention, there is provided a food product quality control system comprising: a support structure; an inspection unit for detecting at least one property of a food product supplied to the inspection unit, the inspection unit being mounted on the support structure; and a conveyor system for conveying a food product through and/or past the inspection unit, the conveyor system being mounted on the support structure; wherein the conveyor system comprises a conveying apparatus carried on a frame, the frame being movably mounted to the support structure such that the frame may move relative to the inspection unit between an operation position, at which the frame is laterally aligned with the inspection unit such that food product may be conveyed through and/or past the inspection unit, and a maintenance position, at which the frame is laterally offset from the inspection unit.

This system mounts an inspection unit and a conveyor system on the same support structure, which ensures high positional accuracy and facilitates installation of the quality control system. In order to address the problem maintaining and cleaning the conveyor and/or the inspection unit with this arrangement, the frame of the conveyor is movably mounted to the support structure so that it can move between its operation position and a maintenance position. In the operation position, the frame is laterally aligned with the inspection unit such that food product may be conveyed through and/or past the inspection unit, i.e. so that the conveyor supplies the food product to the inspection unit for detecting at least one property of a food product. Typically, the inspection unit will be arranged over the conveyor in the operation position. As will be explained in more detail below, a portion of the inspection unit may also or instead extend beneath or within the frame of the conveyor in this operation position. In the maintenance position, the conveyor is laterally offset from the inspection unit so as to increase the room for cleaning and maintaining both the conveyor system and the inspection unit. Preferably, the frame is laterally offset by a distance corresponding to at least 25%, preferably at least 50%, of the horizontal width of the frame, measured across the conveyance direction of the conveyor.

As mentioned above, the present invention relates to a quality control system for food products. The food products may be bulk items, such as pieces of fruit, vegetables, meat or poultry, or may be packaged food items, such as sealed trays of food items or pre-packaged ready-meals. The quality control process is facilitated by the inspection unit, which detects at least one property of a food product supplied to the inspection unit. Example inspection units will be given below, but examples of desirable properties to evaluate as part of a quality control process include: presence of foreign objects such as bones or metal, weight of a food product, seal integrity of a sealed food container, and appearance of a food product.

As will be explained below, various types of conveyor system may be used, including for example belt conveyors, roller conveyors, chain conveyors, and screw conveyors. In all of these examples, the conveyor system comprises a conveyor apparatus carried on a frame. That is, a frame supports the means by which the food product is conveyed. For example, if the conveying apparatus is a conveyor belt entrained about a series of rollers, then this conveyor belt apparatus is mounted on a frame of the conveyor system. The frame is then movably mounted to the support structure such that the frame may move between the operation and maintenance positions, which will thereby move the conveying apparatus as the frame is moved. The frame is therefore a support structure for the conveyor apparatus.

In preferred embodiments of the invention, the frame is slideably mounted on one or more rails of the support structure, wherein preferably the frame is slideable between the operation position and the maintenance position in a direction substantially perpendicular to a conveyance direction of the conveyor system. For example, the support structure may have one, preferably at least two, fixed supporting rails. The frame may mount onto said fixed supporting rails and slide along those rails between the operation and maintenance positions. The supporting rails of the support structure could also not be fixed and may contribute to the movement of the frame between the operation and maintenance positions. Typically the one or more rails of the support structure will be arranged horizontally so that the frame slides horizontally away from the inspection unit, although they could also be mounted with some upward or downward component, e.g. to lower the frame as it slides out from the inspection unit. In preferred cases, the conveyor slides substantially perpendicular to a conveyance direction of the conveyor system, the conveyance direction being the direction along which food product is conveyed past the inspection unit. The conveyor may have, for example, a bend upstream or downstream of the inspection unit. Such perpendicular sliding will encompass horizontal sliding as well as sliding with upwards or downwards components to the lateral movement. Perpendicular sliding is not essential, however, and there may be some sliding along the direction of conveyance. Having the perpendicular sliding of the frame ensures that clearance is achieved with a minimum amount of movement of the conveyor system. Of course, it is not essential for the frame to be slideably mounted on rails of the support structure and other movement mechanisms are anticipated, such as a lever mechanism.

In embodiments in which the frame is slideably mounted on one or more rails of the support structure, further preferably the conveyor system comprises one or more rails of the frame that couple with said one or more rails of the support structure, wherein preferably at least one of said rails of the frame or at least one of said rails of the support structure is eccentrically mounted on a rotatable axis and is rotatable between a locked position, which fixes the frame in place on the support structure, and an unlocked position, which enables the frame to slide between the operation position and the maintenance position. In these embodiments, the frame of the conveyor system has corresponding rails that couple with the rails of the support structure. Depending on the nature of the rails, there may be a single rail that couples with a single of the frame. For example the rail of the support structure may have a groove or channel in its upward facing surface which receives a complementary rail of the support structure. Alternatively, a single rail of the support structure may have grooves or channels in its side surfaces which each receive a complementary rail of the frame. In the preferred embodiment, the support structure comprises two rails which each receive a complementary rail of the frame. It will be appreciated that many different arrangements are possible. As noted above, one or more rails may be eccentrically mounted on a rotatable axis such that rotation of the rail changes the distance between adjacent rails. This may be used to lock and unlock, for example, the rails of the frame to the rails of the support structure. The eccentrically mounted and rotatable rail may have a handle at one end for selectively locking and unlocking the rails to permit sliding to the maintenance position.

The inspection unit may comprise an imaging unit, a weighing unit, a metal detection unit, a gas composition measurement unit and/or a leak detection unit. It will be appreciated that the inspection unit could include multiple in-line units for detecting a number of properties of the food products conveyed by the conveyor. An imaging unit would include a camera for visually inspecting food products, e.g. to identify blood spots on poultry, an X-ray unit for obtaining an X-ray image of a food product and/or identifying the presence of a foreign object such as a bone or bone fragment, as well as other electromagnetic imaging systems. A weighing unit may comprise a weigher arranged beneath a conveyor belt or weight sensitive rollers of a roller conveyor, for example. Gas composition measurement unit would include the use of lasers as spectroscopic light sources for high resolution spectroscopy (HRS), with quantum cascade lasers (QCLs) offering access to the valuable mid infrared (MIR) part of the electromagnetic spectrum. An example of a QCL system may be found in WO 03087787 A1. Leak detection units include systems that apply pressure to sealed food containers and detect variations in gas composition that are produced by modified atmosphere escaping through such breaches. An example of a leak detection unit may be found in WO 2017/191465 A2.

The invention is particularly advantageous when used with an imaging unit, such as an X-ray unit since these units are typically very large and require high positional accuracy, which means that it can be particularly difficult to access the inspection unit and the conveyor for cleaning and maintenance.

In particularly preferred examples, the inspection unit comprises an imaging unit including a radiation source and a radiation detector, and at least part of one of said radiation source and said radiation detector is located inside the frame of the conveyor system when the frame is in the operation position and is laterally offset from the frame of the conveyor when the frame is in the maintenance position. For example, one of said radiation source and said radiation detector may be located over the conveyor and the other located inside the frame of the conveyor behind, for example, a conveying surface such as a conveyor belt. In alternative examples, the radiation source and a radiation detector may be located on opposing sides of the conveyor system, i.e. on opposing sides of the frame; however, placing one of said radiation source and said radiation detector inside the frame increases sensitivity and improves accuracy of detection, since distance to the food product and distance between the source and detector is minimised, while also minimising the height of the quality control system. The arrangement of one of a radiation source and a radiation detector inside the frame makes it particularly difficult to perform maintenance and clean said part of the inspection unit as well as the conveyor system itself. Therefore, the provision of a movable frame that laterally spaces the frame from the inspection unit, e.g. and exposes the part of the inspection unit that was previously located inside the frame, is particularly advantageous.

The inspection unit may be fixedly mounted to the support structure, or the inspection unit may be movably mounted to the support structure. For example, the inspection unit may move in an opposite direction to the conveyor in order to further increase the clearance between the inspection unit and the conveyor system.

While it would be possible to perform all cleaning and maintenance in the maintenance position, in some examples it may be preferable that the frame is removable from the support structure when the frame is in the maintenance position. For example the frame may be removable from the support structure by sliding the frame off the one or more rails of the support structure. That is, the frame may continue sliding beyond the maintenance position (either with or without the release of a catch for holding the frame in the maintenance position) until it is removed entirely from the support structure. In other examples, the frame could be locked to the support structure in the maintenance position by a quick release mechanism that can be activated to, for example, allow the frame to be lifted off the support structure. Typically, removal of the frame from the support structure will require an appropriate lifting apparatus. Providing the frame as removable from the support structure allows for deep cleaning to be performed away from the inspection unit or for more significant maintenance, e.g. replacement of damaged parts. This arrangement may also allow for complete access to the inspection unit for careful cleaning of the often-sensitive elements of the inspection or more significant maintenance requirements. Further still, removal of the frame and conveying apparatus may allow for a replacement frame and conveying apparatus to be provided. This may allow for more simple reconfiguring of the production line or simply avoid downtime while the conveyor system is undergoing remote cleaning and/or maintenance.

In most preferred examples, the conveyor apparatus comprises a plurality of rollers mounted on the frame and a conveyor belt entrained about said plurality of rollers. This may also include a motor mounted within the frame and coupled to the conveyor belt and/or one or more rollers for powering the conveyor belt. The motor may move with the frame to the maintenance position and may require electrical disconnection before movement of the frame to the maintenance position. While a conveyor belt is preferred, other conveyor types would also be possible, such as roller conveyors.

Where a belt conveyor is used, preferably a tensioning roller of said plurality of rollers is movably mounted on the frame, such that said tensioning roller is movable between a belt tension position and a belt release position, wherein in said belt release position the conveyor belt is slackened relative to said belt tension position such that said conveyor belt may be removed from the conveyor system. This further facilitates maintenance of the system. That is, one of the rollers about which the conveyor belt is entrained is movable, i.e. to reduce the perimeter distance about the rollers in order to slacken the conveyor belt. This may allow the conveyor belt may be removed from the conveyor system by lifting it off the frame, i.e. sliding it off the frame in a direction substantially perpendicular to the conveyance direction. Advantageously, the frame may be moved to the maintenance position to allow access to the conveyor system, whereupon the tensioning roller may be moved to the belt release position in order to allow the conveyor belt to be removed. The additional clearance and access provided at the maintenance position ensures that belt removal can be performed quickly and safely.

Various arrangement of the tensioning roller are envisaged, but preferably said tensioning roller is mounted on a retractable frame portion of said frame of the conveyor system, the retractable frame portion moving along a direction substantially perpendicular to the conveyor belt surface between the belt tension position and the belt release position. For example, the tensioning may be mounted between two movable arms which form the retractable frame portion of said frame. One or both arms may be movable perpendicular to the belt surface, i.e. in the direction to reduce the perimeter distance about the rollers, which thereby slackens the belt and allows it to be removed. Preferably, the retractable frame portion is coupled to a main portion of the frame by a mechanical linkage, preferably a two-bar linkage, the mechanical linkage being configured to selectively lock the retractable frame portion in the belt tension position. That is, the mechanical linkage may brace the retractable frame portion in the belt tension position so that the belt is firmly held taught about the plurality of rollers. Operation of the mechanical linkage may break the bracing arrangement of the linkage and permit the roller to move to the belt release position. The mechanical linkage may be operable by a handle, e.g. located at the exterior of the frame, to selectively lock and unlock the retractable frame portion.

In some preferred embodiments, the conveyor system is configured to convey a food product from an input end of the conveyor system to an output end of the conveyor system, and the conveyor system comprises a vertically swinging end portion located at the output end of the conveyor system, wherein the vertically swinging end portion is swingable relative to a main portion of the conveyor system between a first position, at which food product may be output from the conveyor system at first height, and a second position, at which food product may be output from the conveyor system at second height different from the first height. Here, an end portion of the conveyor is movable to access different output positions, i.e. different vertical output positions. This may be useful, for example, for reacting to the property detected by the inspection unit. For example, if a bone is detected in a piece of poultry, this piece may be diverted to a lower output conveyor to return to an appropriate processing station for removal of the bone, while all "good" poultry is directed on to an upper output conveyor for batching an packaging. While conveyor diversion systems have been used in the art previously, these have typically been dedicated conveyor systems that are positioned downstream of the inspection unit. In the present arrangement, the same conveyor that supplies the food product to the inspection unit is able to divert the food product as required. Not only does this reduce the floor space required, but it ensures high accuracy, since a food product with a defect does not need to be tracked across multiple conveyor systems. While a conveyor system of the type described will inherently be more complex as a result of the need to provide an inbuilt diverting mechanism, the ability to move the conveyor system to a maintenance position ensures that sufficient access to the conveyor system can be provided when needed.

Preferably, the vertically swinging end portion comprises a vertically swinging frame portion coupled to a main portion of the frame of the conveyor system, the vertically swinging frame portion swinging relative to said main portion of the frame. Where the conveyor is a belt conveyor, the vertically swinging end portion may comprise at least one swinging roller, said swinging roller being one of said plurality of rollers mounted on the frame (about which the belt is entrained), said swinging roller being located at the output end of the conveyor system and being vertically movable as the vertically swinging end portion swings between the first position and the second position. In this arrangement, the swinging roller defines the end of the conveyor belt and so its movement causes the swinging between the two different output heights and positions the end of the conveyor belt at these two different positions. The swinging roller may be rotatable about an axis located within the frame of the conveyor, wherein the axis is preferably provided by a pivot connecting the vertically swinging frame portion to the main portion of the frame. While preferable the roller may not rotate strictly about an axis, although this is mechanically simpler to achieve.

A particularly preferred implementation of a swinging portion of a conveyor belt involves the vertically swinging end portion comprising two base rollers of the plurality of rollers mounted on the frame, the axis about which the swinging roller rotates being located between said two base rollers. These two base rollers are another two rollers about which the belt is entrained and essentially define the base of the swinging portion of the conveyor system. Preferably said two base rollers are fixedly mounted on said main portion of the frame, and preferably the axis about which the swinging roller rotates is located equidistant between said two base rollers such that movement of the swinging roller as the vertically swinging end portion swings between the first position and the second position substantially does not change the belt tension. This arrangement ensures that movement of the swinging roller does not change the perimeter distance about the entraining rollers of the conveyor belt and so maintains belt tension.

The distance that swinging end portions swings may be configurable to allow adjustment of the speed of operation. That is, smaller swinging distances may be performed more quickly and so may be required in high-throughput systems. This may require two downstream conveyors, i.e. corresponding to the upper and lower output positions, to be placed vertically closer in order to accommodate the smaller swinging distance, or rejected food product may be intended to drop a distance onto a lower conveyor.

One particularly preferred embodiment includes a conveyor belt with the swinging end portion and the tensioning roller described above. Preferably in this embodiment, the tensioning roller is located at the input end of the conveyor system. This arrangement allows for facilitated removal of the belt as described above in combination with the advantages of a swinging end portion of the conveyor.

In accordance with a second aspect of the invention, there is provided a food product quality control system comprising: a support structure; an inspection unit for detecting at least one property of a food product supplied to the inspection unit, the inspection unit being mounted on the support structure; and a conveyor system for conveying a food product through and/or past the inspection unit, the conveyor system being mounted on the support structure; wherein the conveyor system comprises a conveying apparatus carried on a frame, and wherein the conveyor system is configured to convey a food product from an input end of the conveyor system to an output end of the conveyor system using the conveying apparatus, and wherein the conveyor system comprises a vertically swinging end portion located at the output end of the conveyor system, wherein the vertically swinging end portion is swingable relative to a main portion of the conveyor system between a first position, at which food product may be output from the conveyor system at first height, and a second position, at which food product may be output from the conveyor system at second height different from the first height.

As with the above aspect of the invention, the food products may be bulk items, such as pieces of fruit, vegetables, meat or poultry, or may be packaged food items, such as sealed trays of food items or pre-packaged ready-meals. The quality control process is facilitated by the inspection unit, which detects at least one property of a food product supplied to the inspection unit. Example inspection units are given above in relation to the first aspect of the invention, and detect desirable properties such as presence of foreign objects such as bones or metal, weight of a food product, seal integrity of a sealed food container, and appearance of a food product.

As described above in relation to one preferred implementation of the first aspect of the invention, an end portion of the conveyor is movable to access different output positions, i.e. different vertical output positions. This may be useful, for example, for reacting to the property detected by the inspection unit. For example, if a bone is detected in a piece of poultry, this piece may be diverted to a lower output conveyor to return to an appropriate processing station for removal of the bone, while all "good" poultry is directed on to an upper output conveyor for batching an packaging. While conveyor diversion systems have been used in the art previously, these have typically been dedicated conveyor systems that are positioned downstream of the inspection unit. In the present arrangement, the same conveyor that supplies the food product to the inspection unit is able to divert the food product as required. Not only does this reduce the floor space required, but it ensures high accuracy, since a food product with a defect does not need to be tracked across multiple conveyor systems.

As described above, preferably the vertically swinging end portion comprises a vertically swinging frame portion coupled to a main portion of the frame of the conveyor system, the vertically swinging frame portion swinging relative to said main portion of the frame.

Preferably, the conveyor apparatus comprises a plurality of rollers mounted on the frame and a conveyor belt entrained about said plurality of rollers. However, again, other types of conveyor may be used, as described above, such as roller conveyors. Where the conveyor is a belt conveyor, preferably the vertically swinging end portion comprises at least one swinging roller, said swinging roller being one of said plurality of rollers mounted on the frame, said swinging roller being located at the output end of the conveyor system and being vertically movable as the vertically swinging end portion swings between the first position and the second position. In this arrangement, the swinging roller defines the end of the conveyor belt and so its movement causes the swinging between the two different output heights and positions the end of the conveyor belt at these two different positions. The swinging roller may be rotatable about an axis located within the frame of the conveyor, wherein the axis is preferably provided by a pivot connecting the vertically swinging frame portion to the main portion of the frame. While preferable the roller may not rotate strictly about an axis, although this is mechanically simpler to achieve.

A particularly preferred implementation of a swinging portion of a conveyor belt involves the vertically swinging end portion comprising two base rollers of the plurality of rollers mounted on the frame, the axis about which the swinging roller rotates being located between said two base rollers. These two base rollers are another two rollers about which the belt is entrained and essentially define the base of the swinging portion of the conveyor system. Preferably said two base rollers are fixedly mounted on said main portion of the frame, and preferably the axis about which the swinging roller rotates is located equidistant between said two base rollers such that movement of the swinging roller as the vertically swinging end portion swings between the first position and the second position substantially does not change the belt tension. This arrangement ensures that movement of the swinging roller does not change the perimeter distance about the entraining rollers of the conveyor belt and so maintains belt tension.

Where a belt conveyor is used, preferably a tensioning roller of said plurality of rollers is movably mounted on the frame, such that said tensioning roller is movable between a belt tension position and a belt release position, wherein in said belt release position the conveyor belt is slackened relative to said belt tension position such that said conveyor belt may be removed from the conveyor system. This further facilitates maintenance of the system. That is, one of the rollers about which the conveyor belt is entrained is movable, i.e. to reduce the perimeter distance about the rollers in order to slacken the conveyor belt. This may allow the conveyor belt may be removed from the conveyor system by lifting it off the frame, i.e. sliding it off the frame in a direction substantially perpendicular to the conveyance direction. Preferably the tensioning roller is located at the input end of the conveyor system so as to be separate from the swinging end portion of the conveyor system.

BRIEF DESCRIPTION OF THE DRAWINGS

The invention will now be described with reference to the accompanying drawings, of which:

FIGS. 2A to 2C show side views of the food product quality control system shown in FIG. 1 in an operation arrangement, an intermediate arrangement and a maintenance arrangement respectively;

FIGS. 3A and 3B show partial perspective views of the frame of the food product quality control system shown in FIG. 1 at two different positions during movement of the frame on the support structure;

FIGS. 4A to 4C show front views of the frame of the food product quality control system shown in FIG. 1 in a locked and unlocked arrangement and an enlarged detail view respectively;

FIGS. 8A and 8B show perspective views of the conveyor system of the food product quality control system shown in FIG. 7 in two different output arrangements respectively;

DETAILED DESCRIPTION

A first embodiment of the invention will be described with reference to FIGS. 1 to 6B.

Figure 1:
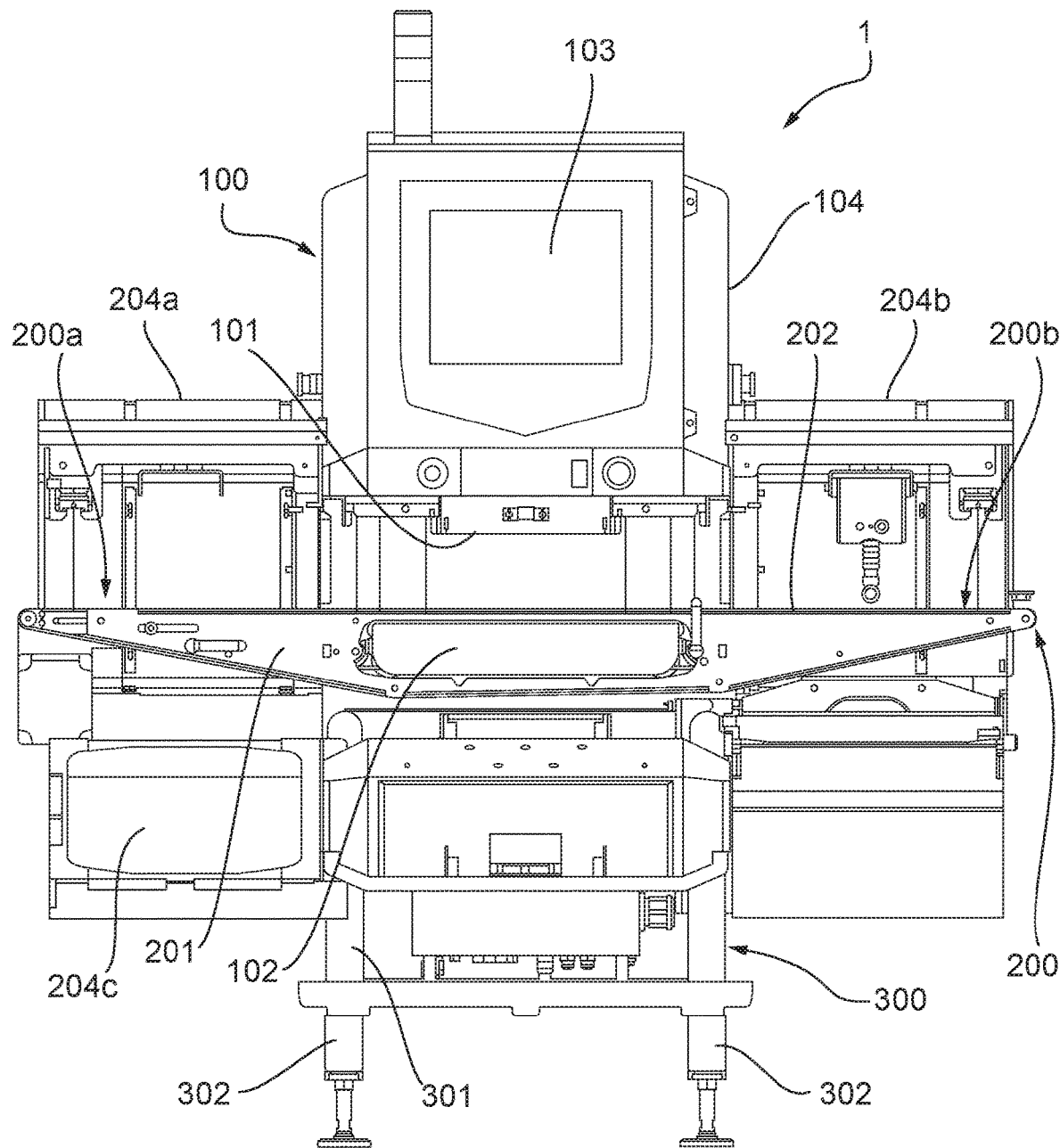
FIG. 1 shows a front view of an embodiment of a food product quality control system.

FIG. 1 shows a front view of a food product quality control system 1. The food product quality control system comprises generally an inspection unit 100 and a conveyor system 200, both mounted on a support structure 300.

The inspection unit 100 is an X-ray unit and comprises an X-ray detector 101, X-ray source 102 and inspection unit display 103. The X-ray detector 101 and the display 103 are housed in an upper system housing 104 supported by the support structure 300. This upper system housing sits over the conveyor system 200, with the X-ray detector 101 being held directly above and facing down towards the conveyor system 200. The X-ray source 102 is located inside the frame of the conveyor system 200, as will be described in more detail below. The X-ray source 102 faces upwards through the belt of the conveyor system 200 and towards the X-ray detector 101.

The conveyor system 200 comprises a frame 201 that holds a conveyor belt 202 entrained about a set of rollers, which will be discussed in more detail below. The frame 201 of the conveyor system 200 is also supported by the support structure 300 and is arranged so that the conveyor 200 conveys food products from an input end 200a, through between the X-ray detector 101 and X-ray source 102, and to an output end 200b on the moving conveyor belt 202. The conveyor system is housed within a lower system housing 204 and the lower system housing extends along the conveyance direction to house input end 200a in an upstream housing portion 204a and to house the output end in a downstream housing portion 204b. The front side of conveyor system 200 may be accessed by opening a door 204c of the lower system housing 204. The lower system housing that surrounds the conveyor 200 between the input end 200a and the output end 200b acts to shield the X-ray radiation generated by the X-ray source 102.

The support structure 300 comprises a single support frame 301 including four legs 302, the support frame 301 extending up into the upper and lower system housings 104, 204. Both the conveyor system 200 and the inspection unit 100 are mounted to this support frame 301 and the arrangement of the conveyor system 200 on the support structure will be described in more detail below.

Figure 2A:
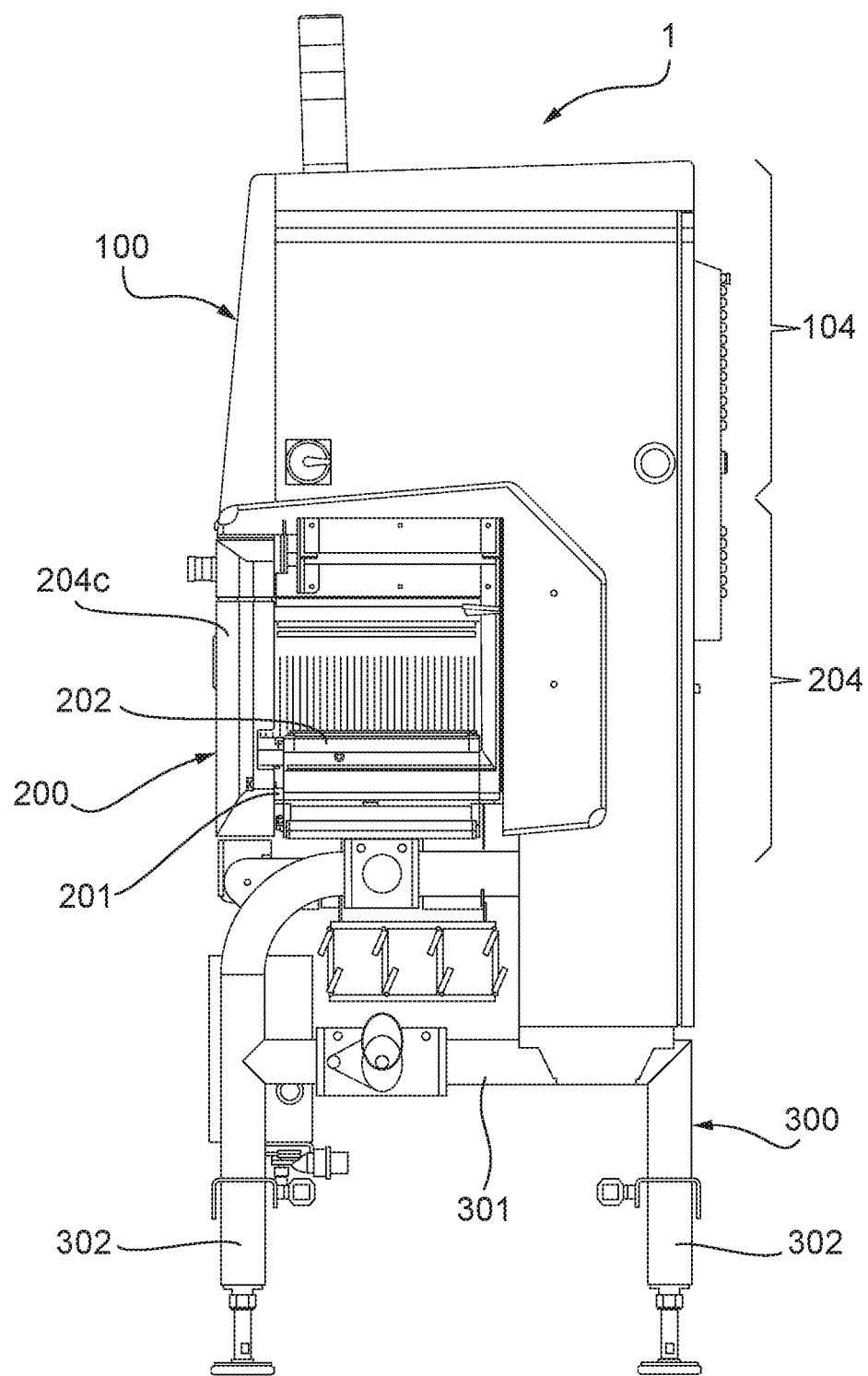
Figure 2B:
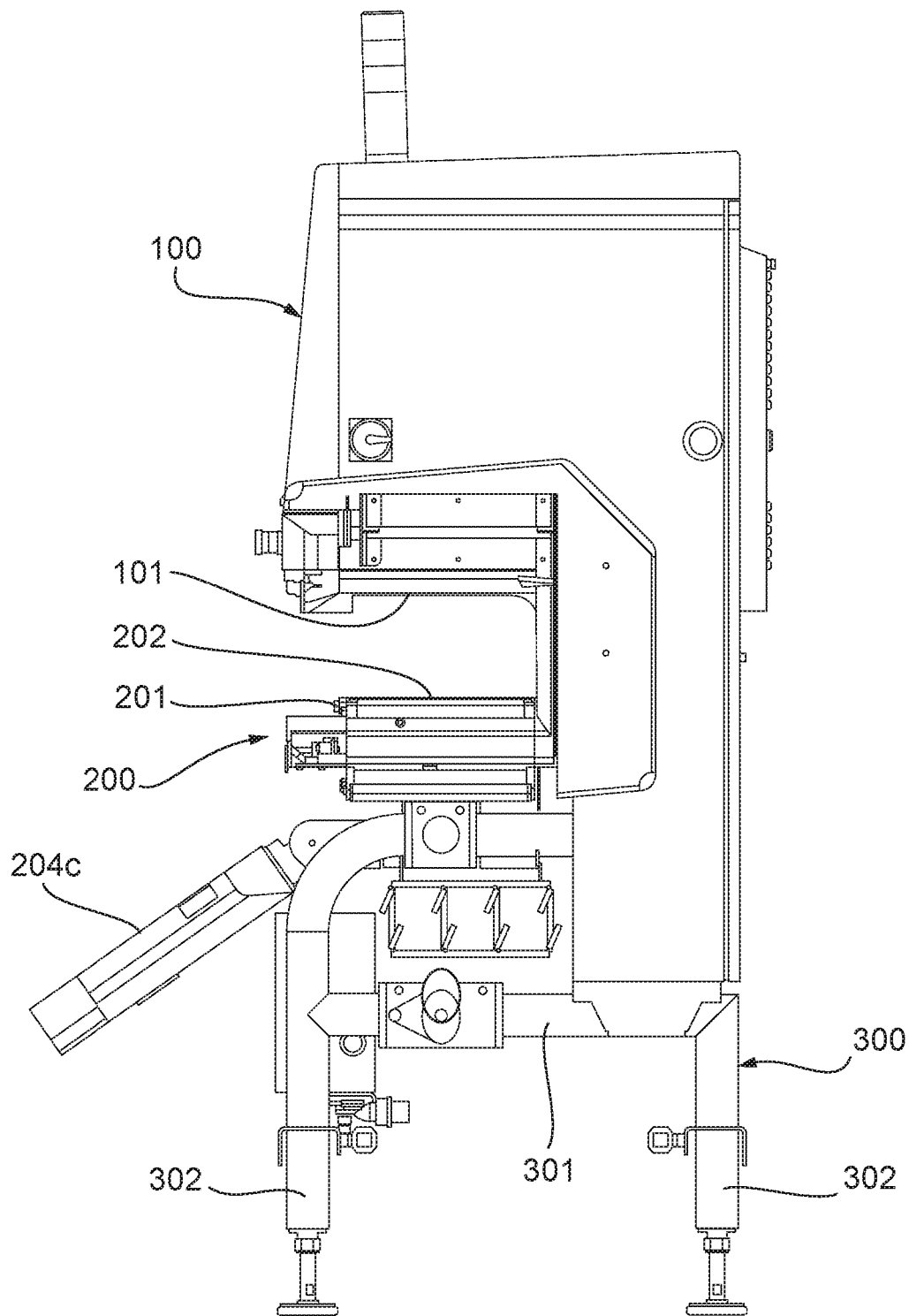

FIGS. 2A to 2C show the food product quality control system 1 in three different side views. In FIG. 2A, the system 1 is in an operation arrangement, with the door 204c on the lower system housing 204 being closed and the frame 201 of the conveyor being located in the operation position such that food product conveyed on the conveyor belt 202 passes between the X-ray detector 101 and X-ray source 102.

In FIG. 2B, the door 204c is opened, exposing the front side of the conveyor system 200 so that an operator may access the conveyor system 200 in order to move it to a maintenance position.

The maintenance position is shown in FIG. 2C. Here, the frame of the conveyor 201, which carries the conveyor belt 202, has been pulled forwards, out from between the X-ray detector 101 and X-ray source 102 and through the opening in the lower system housing 204 provided by the door 204c in the open position. This maintenance position introduces an offset between the frame 201 and the inspection unit 100 as the frame and the belt supported thereby have been moved laterally relative to said inspection unit perpendicular to the conveyance direction. The precise construction of the conveyor system and its mounting on the support structure 300 will now be described in more detail with reference to FIGS. 3A to 4C in order to demonstrate the arrangement that enables this movement between operation and maintenance positions.

Figure 3A:
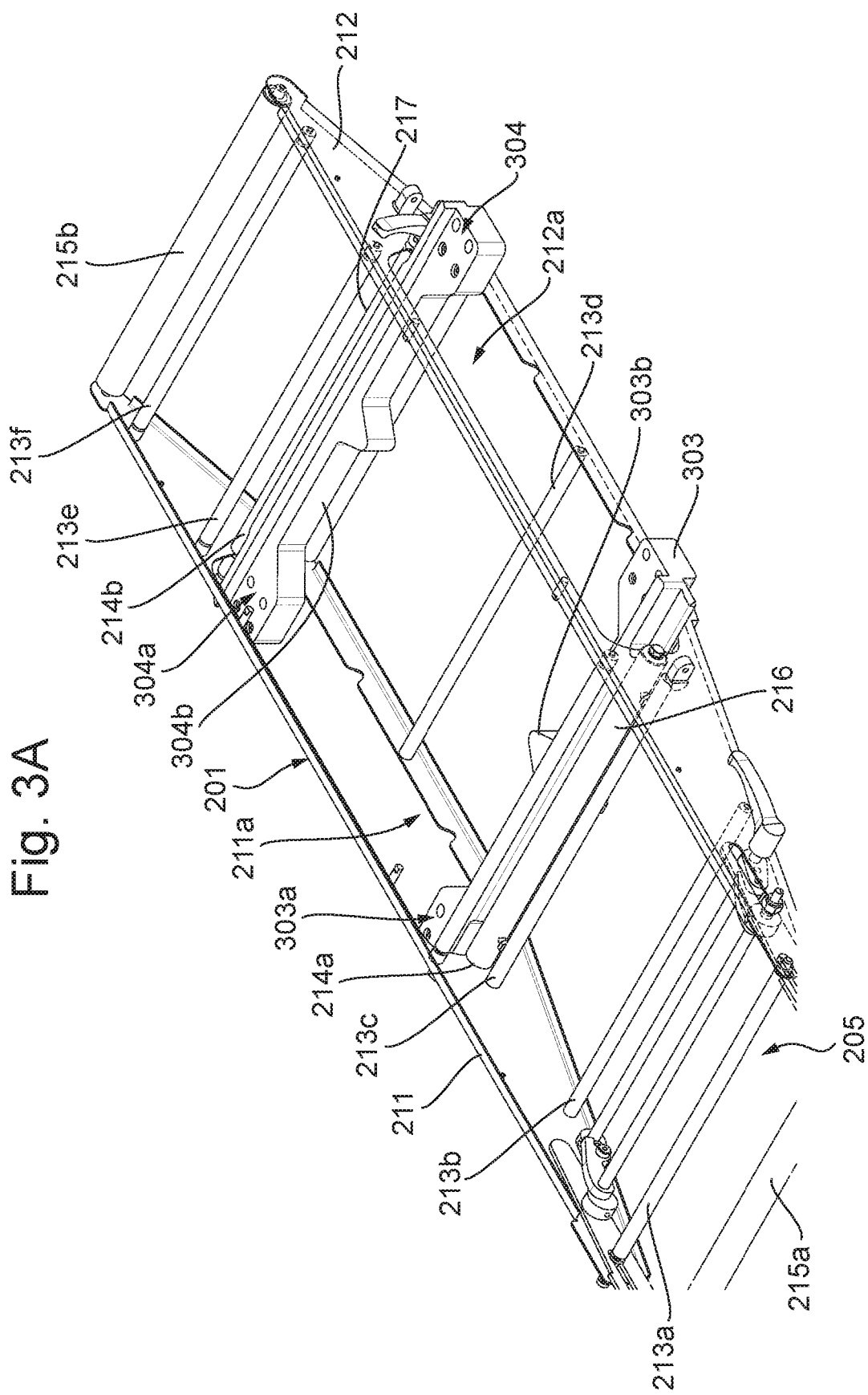
Figure 5A:
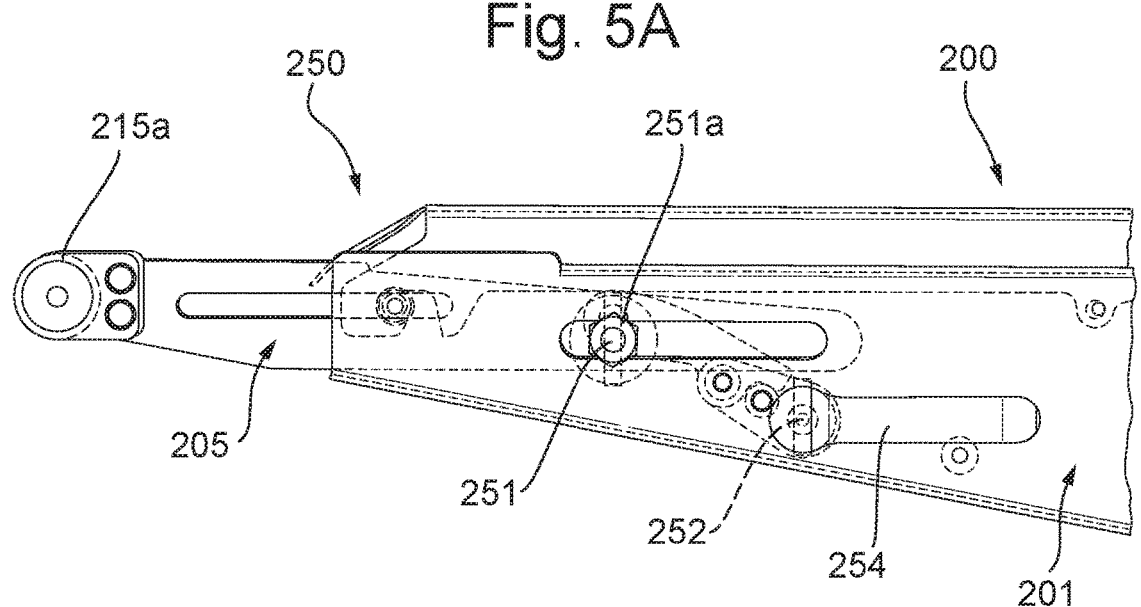
FIGS. 5A and 5B show a front view and perspective view respectively of the frame of the food product quality control system shown in FIG. 1 in a belt tension arrangement.
Figure 5B:
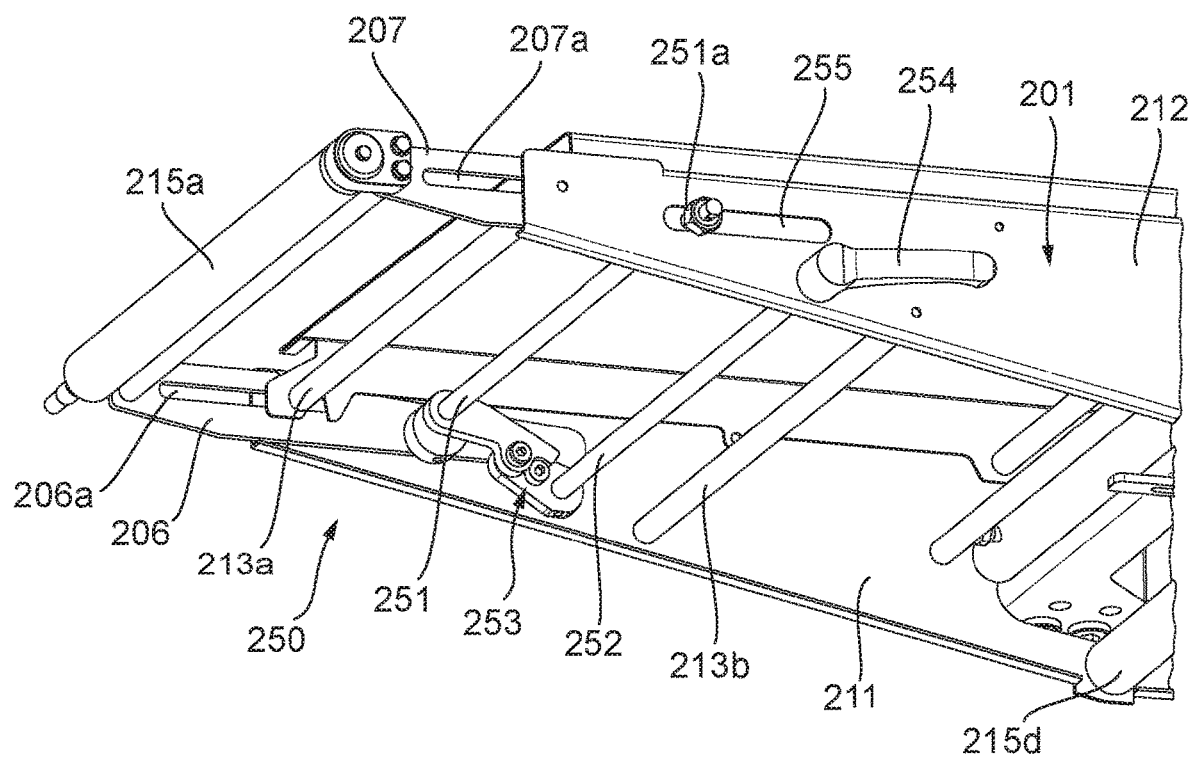

FIGS. 3A and 3B show the frame 201 of the conveyor system 200 and omit the conveyor belt 202 and the rest of the system 1 except for two support rails 303, 304 of the support structure 300, to which the frame 201 is mounted. FIGS. 4A and 4B show a partial front view of the frame 201.

The frame 201 comprises opposing side plates 211, 212 that define the rear side and the front side of the conveyor 200 respectively. The two side plates 211, 212 are connected to one another by a series of connecting rods 213a-213f which extend from one side plate to the other across the width of the conveyor, with each rod being located at a different position along the conveyance direction of the conveyor.

Mounted on the frame are four rollers 215a-215d, about which the conveyor belt 202 (not shown in FIGS. 3A and 3B) is entrained. These four rollers 215a-215d define the extent of the conveyor belt 202. A first roller 215a is located at the input end 200a of the conveyor system and defines the leading edge of the conveyor. This roller 215a is mounted on a retractable frame portion 205 of the frame 201, which will be described in more detail below. The first roller 215a extends across the width of the conveyor 200 between the rear side and the front side of the conveyor 200. A second roller 215b is located at the output end 200b of the conveyor system 200 and defines the trailing edge of the conveyor. In this embodiment, the second roller extends between the opposing side plates 211, 212 and rotates about a fixed axis; although, a different embodiment will be described further below in which this second roller is translationally movable in order to swing the output end of the conveyor up and down. The conveyor belt extends from the first roller 215a to the second roller 215b to define the substantially flat conveying surface that conveys food products through the inspection unit. The third and fourth rollers 215c, 215d are mounted lower than the first and second rollers and define the return path for the conveyor belt to the first roller 215a. These third and fourth rollers 215c, 215d extend between the opposing side plates 211, 212 and rotate about a respective fixed axis. The spacing of these rollers lower than the first and second rollers 215a, 215b defines a volume inside the frame between the upper and lower surface of the conveyor belt 202. As will be described in more detail below, this volume inside the belt receives the X-ray source 102, and also contains the conveyor belt motor (not shown).

A respective opening 211a, 212a is provided in each side plate 211, 212 of the frame 201. This opening extends along a significant portion of the length of the conveyor 200, substantially between the third and fourth rollers 215c, 215d and provides access to the volume inside the frame between the upper and lower surface of the conveyor belt 202. When the frame 201 is mounted to the support structure 300, first and second rails 303, 304 of the support structure extend through the opening 211a in the first side plate 211, through the volume inside the frame between the upper and lower surface of the conveyor belt 202, and out of the opening 212a in the second side plate 212. The first rail 303 extends through the opening proximate the fourth roller 215d, towards the input end of the conveyor, and the second rail 304 extends through the opening proximate the third roller 215c, towards the output end of the conveyor, such that a space between the two rails exists between the upper and lower surface of the conveyor belt. Each rail 303, 304 is fixedly mounted at its rear end, i.e. the end opposite the door 204c of the lower housing 204, to the frame 301 of the support structure 300 by bolts received through a series of bolt holes 303a, 304a in each rail 303, 304. The first rail defines a mount portion 303b that faces a mount portion 304b of the second rail, which together receive and support the X-ray radiation source 102 in the volume inside the frame between the upper and lower surface of the conveyor belt 202.

The input-side rail 303 additionally defines a lower flange 303c along the length of the rail. The flange extends out towards the input end of the conveyor. Similarly, the output-side rail 304 defines a lower flange 304c along the length of the rail. The flange extends out towards the output end of the conveyor. Corresponding rails 216, 217 are provided on the frame 201. The rail 216 extends between the opposing side plates 211, 212 adjacent the openings 211a, 212a towards the input end of the conveyor so that it will sit on the flange 303c of the rail 303. The rail 217 extends between the opposing side plates 211, 212 adjacent the openings 211a, 212a towards the output end of the conveyor so that it will sit on the flange 303c of the rail 303. The support rails 303, 304 thereby receive the rails 216, 217 of the frame 201 and support the conveyor 200 in its position beneath the X-ray detector 101.

FIG. 3B shows the frame as it has been moved away from the operation position shown in FIG. 3A towards the maintenance position. Here, the frame has been slid partially off the support rails 303, 304. In particular, the rails 216, 217 of the frame 201 allow the frame to slide along the support rails 303, 304 of the support structure 300.

In order to prevent the frame from sliding on the support rails 303, 304 during operation, a locking mechanism is provided, which locks the rails of the frame 216, 217 to the support rails. Operation of the locking mechanism can be more clearly seen in FIGS. 4A to 4C.

FIG. 4A shows the frame 201 in its locked position. The rail 217 comprises a rail body 217b, most clearly seen in FIG. 4C, which is the cylindrical portion that extends between the opposing side plates 211, 212. This rail body is rotatable and is eccentrically mounted on a rotation axis 217c. In the locked position, the rail body 217b is positioned so that the thicker side of the rail body 217b faces towards the support rail 304. This position minimises the distance between the two rails 216, 217 and clamps the frame onto the complementary surfaces of the support rails 303, 304. A handle 217a is accessible from the front side of the conveyor and is operable to rotate the rail body 217b in order to unlock the frame by increasing the distance between the two rails 216, 217. The unlocked position is shown in FIG. 4B. In this unlocked position, the frame may slide towards the maintenance position, as described above.

One important aspect of conveyor belt cleaning and maintenance is removal of the conveyor belt 202. The present embodiment features a belt tension and release system 250, which will now be described with reference to FIGS. 5A to 6B.

The belt tension and release system 250 is located at the input end of the conveyor 200. The first roller 215a is mounted on a retractable frame portion 205 of the frame 201. In particular, the roller 215a extends between arms 206, 207. The first arm 206 is slideably mounted on the first side plate 211 of the frame 201 and the second arm 207 is slideably mounted on the second side plate 212. The arms are able to slide along their respective side plate along the direction of conveyance in order to shorten the length of the conveyor, i.e. to decrease the distance between the first roller 215a and the second roller 215b, in order to slacken the conveyor belt 202 entrained about the rollers. Each arm 206, 207 has a slot 206a, 207a extending along a part of its length proximate the roller 215a and through which a respective end of the first connecting rod 213a passes as it connects to the corresponding side plate 211, 212. These slots 206a, 206b help support the sliding frame portion 205 on the connecting rod 213a and allow it to slide relative thereto.

An end of each arm 205, 207 distal from the roller 215a is connected to a movable rod 251 that extends across the width of the conveyor between the side plates 211, 212 of the frame 201. The movable rod 251 is coupled to each arm and extends therethrough and is passes through a respective slot 255 in each side plate 211, 212 (with only the slot in the front side plate 212 being visible in the Figures). The movable rod 251 is retained in the two slots 255 by a nut 251a on each end of the rod, which prevents the end of the rod from passing through the slot 255. Each slot 255 extends along the conveyance direction and so allows the rod to slide along the length of the conveyor as the retractable frame portion 205 retracts in order to shorten the length of the conveyor.

A rod 252 extends between the first and second side plates 211, 212 of the frame 201 and is rotatably mounted to these side plates so that it may rotate about its axis. A handle 254 is accessible from the front side plate 212 of the frame 201 in order to effect rotation of this rod 252. This rotatable rod 252 is coupled at each end to the movable bar 251 by a two-bar linkage 253. In the belt tension position, shown in FIGS. 5A and 5B, the two-bar linkage connecting the movable rod 251 to the rotatable rod 252 braces the movable rod 251 in position with the retractable frame portion 205 extended. This maximises the distance between the first and second rollers 215a, 215b and so maximises the perimeter distance about the four rollers 215a-215d in order to hold the belt taught.

Figure 6A:
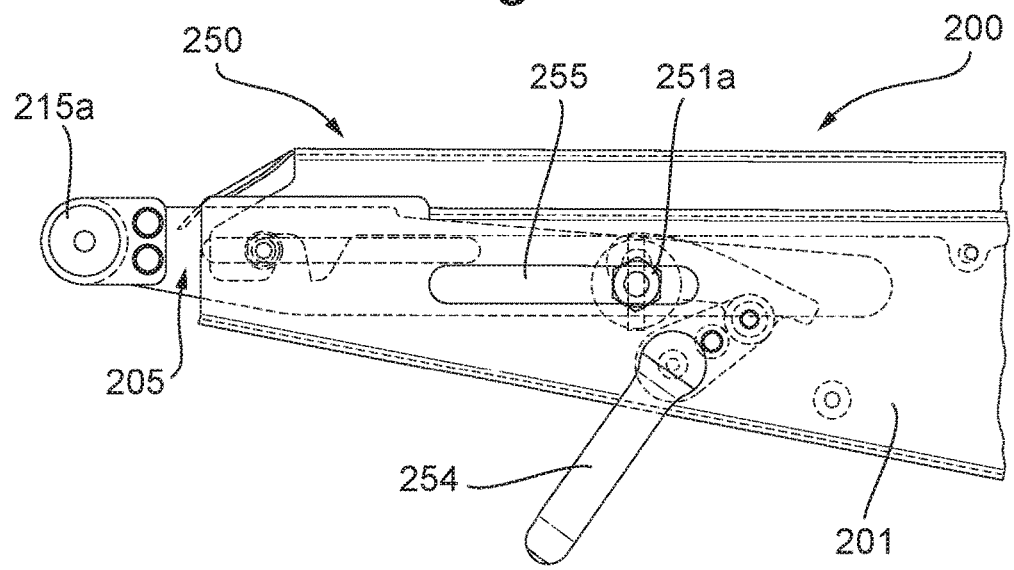
FIGS. 6A and 6B show a front view and perspective view respectively of the frame of the food product quality control system shown in FIG. 1 in a belt release arrangement.
Figure 6B:
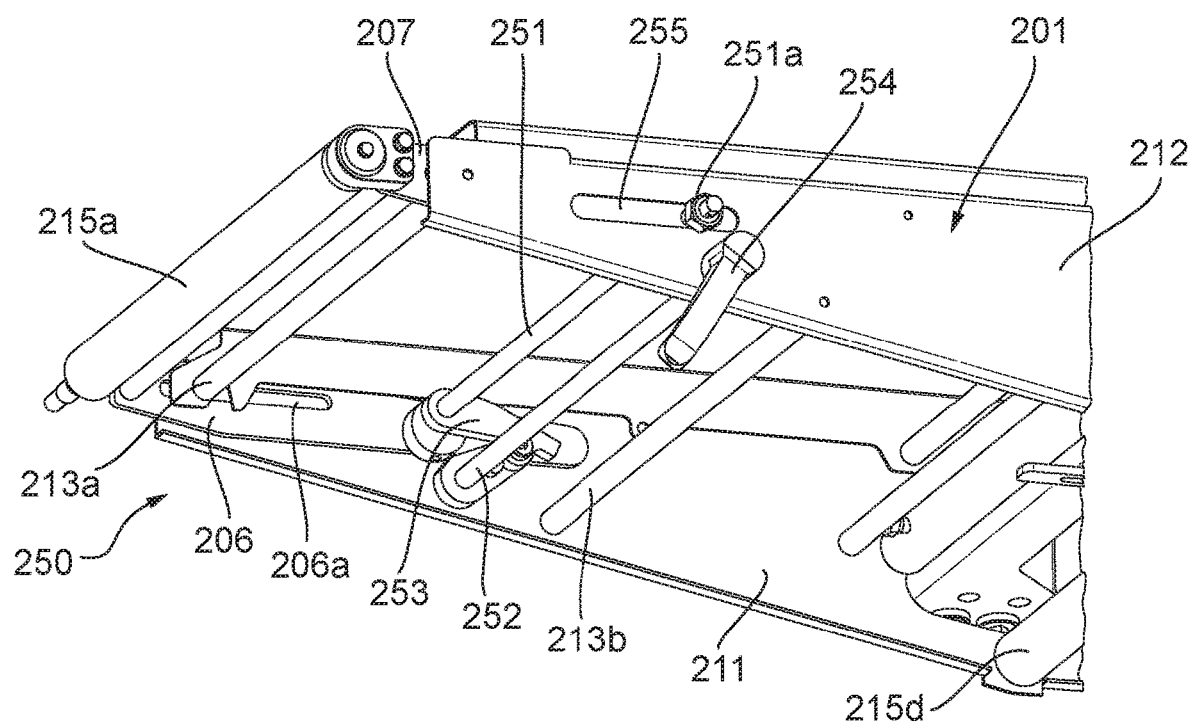

When the rotatable rod 252 is rotated by operation of the handle 254, the alignment of the two-bar linkage is broken and the two-bar linkage pulls the movable rod 251 causing it to slide in the slot 255 and causing the retractable frame portion 205 to retract as the arms 205, 206 slide along the conveyance direction. This decreases the perimeter distance about the four entraining rollers 215a-215d and so slackens the conveyor belt 202 so that it may be removed from the conveyor system 200. This belt release position, i.e. in which the retractable frame portion 205 has retracted, is shown in FIGS. 6A and 6B. In this position, the conveyor belt 202 (not shown in these Figures) may be lifted off or placed on the conveyor system 200 by moving it horizontally relative to the frame and rollers.

A second embodiment of the invention will now be described with reference to FIGS. 7 to 10.

Figure 7:
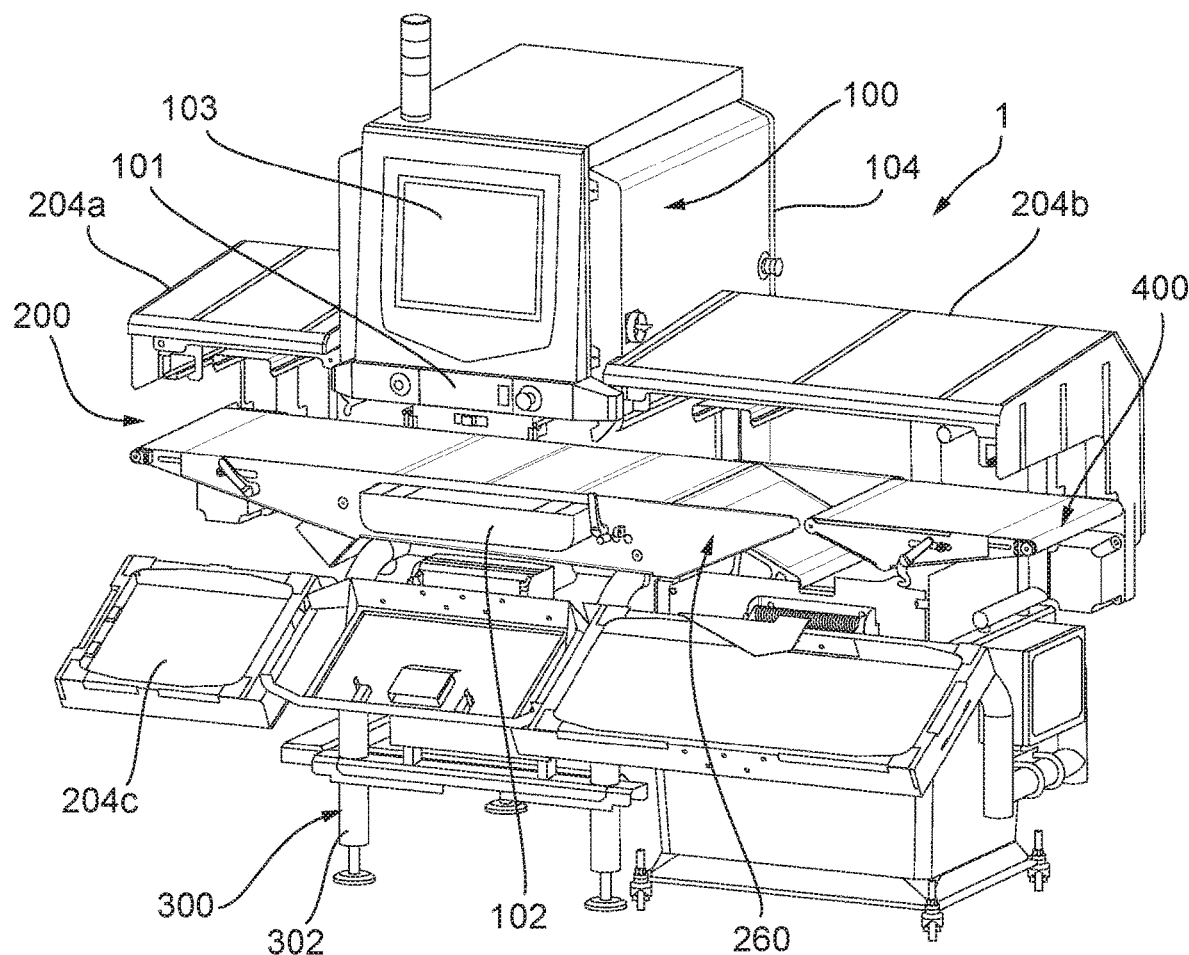
FIG. 7 shows a perspective view of an embodiment of a food product quality control system.

FIG. 7 is a front perspective view of the food product quality control system 1. This system is largely the same as the system described above with respect to FIGS. 1 to 6C and the same reference numerals have been used for corresponding elements of the system. Where this food product quality control system differs from the previous embodiment is in the construction of the output end of the conveyor system 200. In particular, the output end of the conveyor system 200 features a vertically swinging end portion 260, which enables the system to output a food product from the conveyor 200 at two different heights. The system further comprises a separate downstream conveyor system 400 arranged to receive food product output at a first height. This system may receive food product deemed acceptable for packaging, for example, and may convey these food products towards a downstream batching and packaging system. This downstream conveyor system is relatively short in comparison with the conveyor system 200 and is encompassed within an extended downstream housing portion 204b and the door 204c is likewise extended to enclose the conveyor 200 in the housing during operation, while allowing access during cleaning or maintenance. This downstream conveyor system 400 may pass food product out of the quality control system 1 and on to appropriate conveying means in the rest of the system.

Not visible in FIG. 7 is a reject handling portion of the system, which receives food product output at a second height, lower than the first height. That is, the vertically swinging end portion 260 may swing down from a position in which it conveys food product onto the downstream conveyor system 400 in order to deposit rejected food product in a reject handling portion of the system. In a simple example, this reject handling portion could simply be a bin for collecting rejected food products, but preferably a second downstream conveyor would be provided at the lower output height for conveying rejected food products to reject processing. For example, if food product is rejected for having a bone fragment in it, this may be conveyed to an operator for manual removal of the bone fragment, or rerouted back through bone piece removal systems.

The vertically swinging end portion 260 of the conveyor system 200 will now be described in more detail with reference to FIGS. 8A to 10.

FIGS. 8A and 8B show front perspective views of the conveyor system 200 with a vertically swinging end portion 260. The input end of the conveyor comprises a retractable frame portion 205 for providing belt tension and belt release configurations, as described above, and the conveyor 200 has the same mounting arrangement comprising openings 211a, 212a, through the side plates 211, 212 of the frame 201 and in which the support rails 303, 304 are received to support the conveyor on rails 216, 217. The vertically swinging end portion 260 is located at the output end of the conveyor 200 and is movable between a first portion, shown in FIG. 8A, in which the conveyor belt 202 is substantially flat between the input and output ends so that food product is output at a first height, and a second position, shown in FIG. 8B, in which the conveyor belt 202 slopes downward at the vertically swinging end portion 260 so that food product is output at a second height lower than the first height.

Figure 9A:
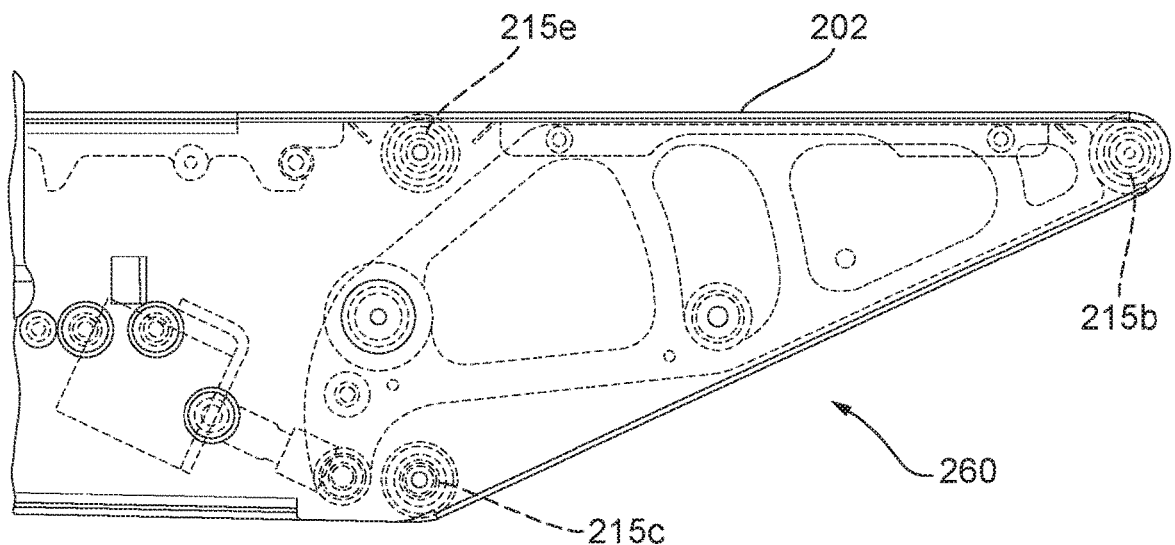
FIGS. 9A and 9B show enlarged front views of the conveyor system of the food product quality control system shown in FIG. 7 in two different output arrangements respectively.
Figure 9B:
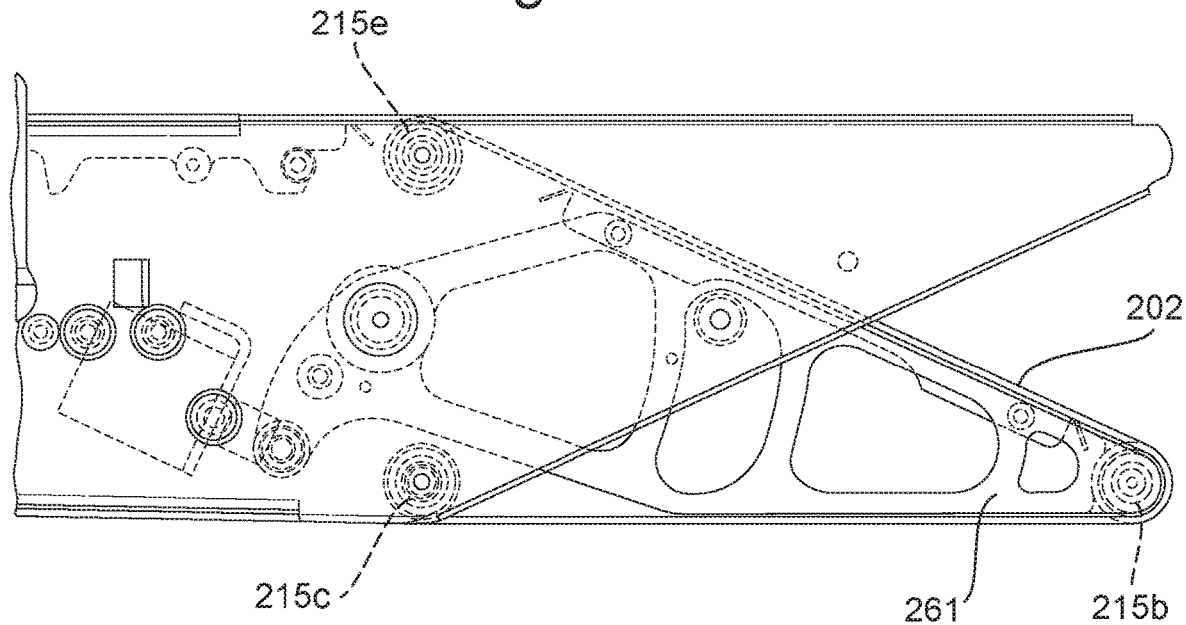
Figure 10:
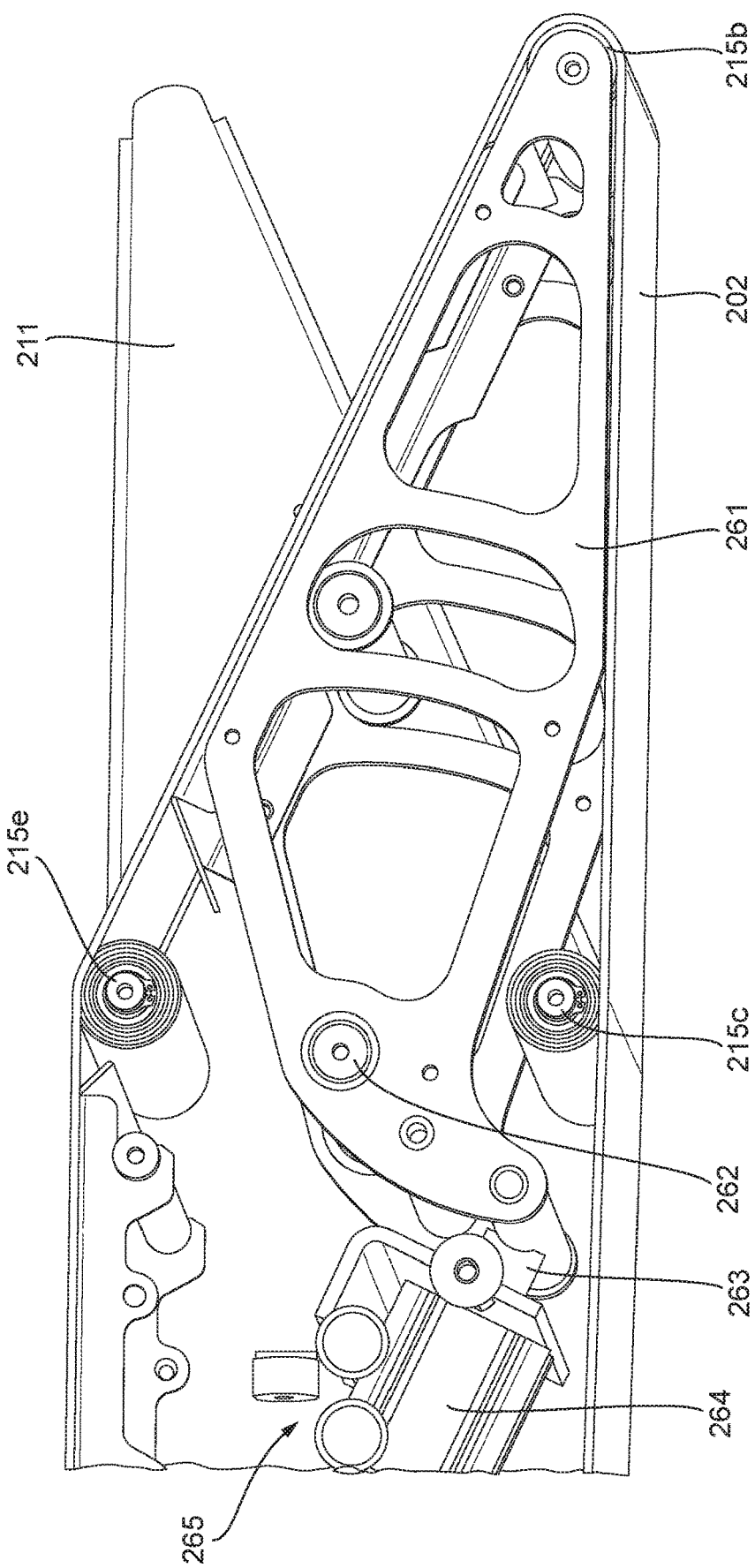
FIG. 10 shows a partial perspective view of the conveyor system of the food product quality control system shown in FIG. 7.

The vertically swinging end portion 260 is shown in more detail in FIGS. 9A, 9B and 10. FIGS. 9A and 9B are enlarged views of the vertically swinging end portion 260 at the first and second positions respectively and show the front side plate 212 semi-transparent to reveal the inner elements of the swinging end portion 260. FIG. 9C is an enlarged perspective view of the vertically swinging end portion 260 with the front side plate 212 omitted.

As shown in these Figures, the vertically swinging end portion 260 comprises a vertically swinging frame portion 261. This vertically swinging frame portion 261 is an arm of the frame 2019 that is rotatably coupled to the main portion of the frame, i.e. the side plates 211, 212, by a pivot 262 that extends horizontally between the two side plates 211, 212. The end of the vertically swinging frame portion 261 distal from the pivot holds the second roller 215b, being one of the rollers about which the conveyor belt 202 is entrained. A pneumatic actuator 264 is mounted inside the frame 201 by mountings 265 and the actuating arm is coupled to the vertically swinging frame portion 261 at a handle section 263 that is offset from the pivot 262. The linear motion of the actuating arm of the pneumatic actuator 264 is operable to rotate the vertically swinging frame portion 261 about the pivot 262 by moving the handle section 263. Actuation of the pneumatic actuator 264 causes the vertically swinging frame portion 261 to rotate between the first position, in which the second roller 215b is level with the first roller 215a at the input end so that the conveyor belt 202 is substantially flat between the input and output ends, and a second position, at which the second roller 215b is level with the third and fourth rollers 215c, 215b so that the conveyor belt 202 slopes down towards the output end.

In order to ensure that the conveyor belt remains substantially flat between the input end and the vertically swinging end portion 260 when the frame portion 261 is swung down, and only slopes down at the vertically swinging end portion 260, a fifth roller 215e is provided level with the first roller 215a and substantially in the same vertical plane as the pivot 262. This fifth roller is rotatably mounted on a fixed axis extending between the side plates 211, 212 of the frame 201. The fifth roller 215e, the pivot 262, and the third roller 215c are each arranged extending across the conveyance direction of the conveyor substantially in vertical alignment with one another. In this arrangement, the belt is entrained, in order, about the first roller 215a, then the fifth roller 215e, then the swinging second roller 215b, then the third roller 215c and then the fourth roller 215d, before returning to the first roller 215a. Not only does the fifth roller 215e ensure that the conveyor belt remains level between the input end and the vertically swinging end portion 260, but the fifth roller 215e and the third roller 215c act as base rollers of the vertically swinging end portion, with the pivot being mounted equidistant between two rollers 215c, 215e. This ensures that movement of the swinging second roller 215b does not change the perimeter distance about the entraining rollers 215a-215e of the conveyor belt and so maintain belt tension.

The actuator 264 may be configured to change the length by which the arm moves during actuation. This may be used to change the distance that the vertically swinging frame portion 261 swings. Preferably, it is configurable to change the amount the vertically swinging frame portion 261 swings down from the position in which the first, fifth and second rollers 215a, 215e, 215b are level. A smaller swinging distance may be performed more quickly and so may be required in high-throughput systems.

The invention claimed is:

1. A food product quality control system comprising:
   a support structure;
   an inspection unit for detecting at least one property of a food product supplied to the inspection unit, the inspection unit being mounted on the support structure; and
   a conveyor system for conveying a food product through and/or past the inspection unit, the conveyor system being mounted on the support structure;
   wherein the conveyor system comprises a conveying apparatus carried on a frame, the frame being movably mounted to the support structure such that the frame may move relative to the inspection unit between an operation position, at which the frame is laterally aligned with the inspection unit such that food product may be conveyed through and/or past the inspection unit, and a maintenance position, at which the frame is laterally offset from the inspection unit.

2. A food product quality control system according to claim 1, wherein the frame is slideably mounted on one or more rails of the support structure.

3. A food product quality control system according to claim 2, wherein the conveyor system comprises one or more rails of the frame that couple with said one or more rails of the support structure.

4. A food product quality control system according to claim 1, wherein said inspection unit comprises an imaging unit, a weighing unit, a metal detection unit, a gas composition measurement unit and/or a leak detection unit.

5. A food product quality control system according to claim 1, wherein at least part of the inspection unit is located inside the frame of the conveyor system when the frame is in the operation position, and wherein said part of the inspection unit is laterally offset from the frame of the conveyor when the frame is in the maintenance position.

6. A food product quality control system according to claim 5, wherein said inspection unit comprises an imaging unit including a radiation source and a radiation detector, and wherein at least part of one of said radiation source and said radiation detector is located inside the frame of the conveyor system when the frame is in the operation position and is laterally offset from the frame of the conveyor when the frame is in the maintenance position.

7. A food product quality control system according to claim 1, wherein the frame is removable from the support structure when the frame is in the maintenance position.

8. A food product quality control system according to claim 7, wherein the frame is slideably mounted on one or more rails of the support structure.

9. A food product quality control system according to claim 1, wherein the conveyor apparatus comprises a plurality of rollers mounted on the frame and a conveyor belt entrained about said plurality of rollers.

10. A food product quality control system according to claim 9, wherein a tensioning roller of said plurality of rollers is movably mounted on the frame, such that said tensioning roller is movable between a belt tension position and a belt release position, wherein in said belt release position the conveyor belt is slackened relative to said belt tension position such that said conveyor belt may be removed from the conveyor system.

11. A food product quality control system according to claim 10, wherein said tensioning roller is mounted on a retractable frame portion of said frame of the conveyor system, the retractable frame portion moving along a direction substantially perpendicular to the conveyor belt surface between the belt tension position and the belt release position.

12. A food product quality control system according to claim 11, wherein the retractable frame portion is coupled to a main portion of the frame by a mechanical linkage, the mechanical linkage being configured to selectively lock the retractable frame portion in the belt tension position.

13. A food product quality control system according to claim 12, wherein the mechanical linkage is operable by a handle to selectively lock and unlock the retractable frame portion.

14. A food product quality control system according to claim 1, wherein the conveyor system is configured to convey a food product from an input end of the conveyor system to an output end of the conveyor system, and wherein the conveyor system comprises a vertically swinging end portion located at the output end of the conveyor system, wherein the vertically swinging end portion is swingable relative to a main portion of the conveyor system between a first position, at which food product may be output from the conveyor system at first height, and a second position, at which food product may be output from the conveyor system at second height different from the first height.

15. A food product quality control system according to claim 14, wherein the vertically swinging end portion comprises a vertically swinging frame portion coupled to a main portion of the frame of the conveyor system, the vertically swinging frame portion swinging relative to said main portion of the frame.

16. A food product quality control system according to claim 14, wherein the conveyor apparatus comprises a plurality of rollers mounted on the frame and a conveyor belt entrained about said plurality of rollers and wherein the vertically swinging end portion comprises at least one swinging roller, said swinging roller being one of said plurality of rollers mounted on the frame, said swinging roller being located at the output end of the conveyor system and being vertically movable as the vertically swinging end portion swings between the first position and the second position.

17. A food product quality control system according to claim 16, wherein said swinging roller is rotatable about an axis located within the frame of the conveyor.

18. A food product quality control system comprising:
    a support structure;

an inspection unit for detecting at least one property of a food product supplied to the inspection unit, the inspection unit being mounted on the support structure; and a conveyor system for conveying a food product through and/or past the inspection unit, the conveyor system being mounted on the support structure;

wherein the conveyor system comprises a first conveyor belt carried on a frame, and wherein the conveyor belt is configured to convey a food product from an input end of the conveyor system to an output end of the conveyor system, and wherein the first conveyor belt comprises a vertically swinging end portion located at the output end of the conveyor system, wherein the vertically swinging end portion is swingable relative to a main portion of the first conveyor belt, incorporated in the same first conveyor belt as the swinging end portion, between a first position, at which food product may be output from the first conveyor belt at first height, and a second position, at which food product may be output from the first conveyor belt at second height different from the first height.

19. A food product quality control system according to claim 18, wherein the vertically swinging end portion comprises a vertically swinging frame portion coupled to a main portion of the frame of the conveyor system, the vertically swinging frame portion swinging relative to said main portion of the frame.

20. A food product quality control system according to claim 18, wherein the first conveyor belt comprises a plurality of rollers mounted on the frame and a belt entrained about said plurality of rollers, and wherein the vertically swinging end portion comprises at least one swinging roller, said swinging roller being one of said plurality of rollers mounted on the frame, said swinging roller being located at the output end of the conveyor system and being vertically movable as the vertically swinging end portion swings between the first position and the second position.

* * * * *